United States Patent
Lindh et al.

(10) Patent No.: US 7,236,826 B2
(45) Date of Patent: Jun. 26, 2007

(54) SYSTEM AND METHOD FOR GRAPHICALLY CONFIGURING LEADS

(75) Inventors: Par Lindh, Little Canada, MN (US); James Kalgren, Lino Lakes, MN (US); Rene H. Wentkowski, White Bear Lake, MN (US); John Lockhart, San Ramon, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/738,400

(22) Filed: Dec. 15, 2000

(65) Prior Publication Data

US 2002/0077669 A1  Jun. 20, 2002

(51) Int. Cl.
  *A61N 1/00* (2006.01)
  *A61B 5/04* (2006.01)
(52) U.S. Cl. .......................................... 607/27; 600/373
(58) Field of Classification Search ................... 607/18, 607/25, 26, 27, 116, 122; 600/515, 118, 600/522, 523, 527, 528, 373, 374, 423, 424
See application file for complete search history.

(56) References Cited

U.S. PATENT DOCUMENTS

| | | | | |
|---|---|---|---|---|
| 5,312,448 A * | 5/1994 | Hognelid et al. | ............. | 607/13 |
| 5,411,528 A * | 5/1995 | Miller et al. | ................ | 307/127 |
| 5,433,198 A * | 7/1995 | Desai | ........................... | 600/374 |
| 5,480,422 A * | 1/1996 | Ben-Haim | ................... | 600/439 |
| 5,620,472 A | 4/1997 | Rahbari | ....................... | 607/27 |
| 5,697,959 A | 12/1997 | Poore | ........................... | 607/32 |
| 5,713,937 A * | 2/1998 | Nappholz et al. | ............. | 607/30 |
| 5,803,084 A * | 9/1998 | Olson | ......................... | 600/512 |
| 5,891,179 A | 4/1999 | Er et al. | ........................ | 607/27 |
| 6,052,624 A * | 4/2000 | Mann | ........................... | 607/46 |
| 6,088,618 A | 7/2000 | Kerver | ......................... | 607/30 |
| 6,101,415 A | 8/2000 | Er et al. | ........................ | 607/27 |
| 6,400,981 B1 * | 6/2002 | Govari | ......................... | 600/509 |
| 6,445,952 B1 * | 9/2002 | Manrodt et al. | ............... | 607/28 |
| 7,003,349 B1 * | 2/2006 | Andersson et al. | ............ | 607/27 |

\* cited by examiner

*Primary Examiner*—Sang Y. Paik
(74) *Attorney, Agent, or Firm*—Schwegman, Lundberg, Woessner & Kluth, P.A.

(57) ABSTRACT

Systems and methods are provided for graphically configuring leads for a medical device. According to one aspect, the system generally comprises a medical device and a processing device, such as a programmer or computer, adapted to be in communication with the medical device. The medical device has at least one lead with at least one electrode in a configuration that can be changed using the processing device. The processing device provides a graphical display of the configuration. In one embodiment, the graphical display graphically represents, illustrates or displays the lead(s), the electrode(s), a pulse polarity, and a vector. According to another aspect, the method generally comprises receiving information for a medical device having at least one lead with at least one electrode in a configuration, and presenting a graphical representation of the configuration on a display. According to other aspects, a device and a computer-readable medium encoded with a software program for providing a graphical display of a lead configuration for an implantable medical device are also provided herein.

57 Claims, 25 Drawing Sheets

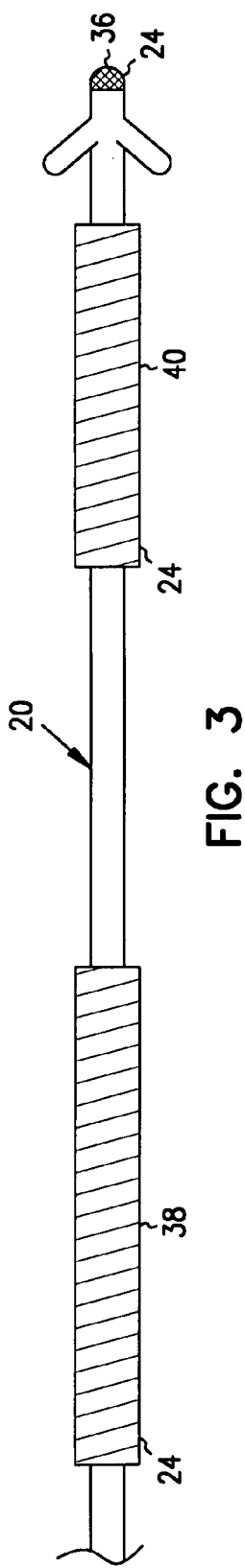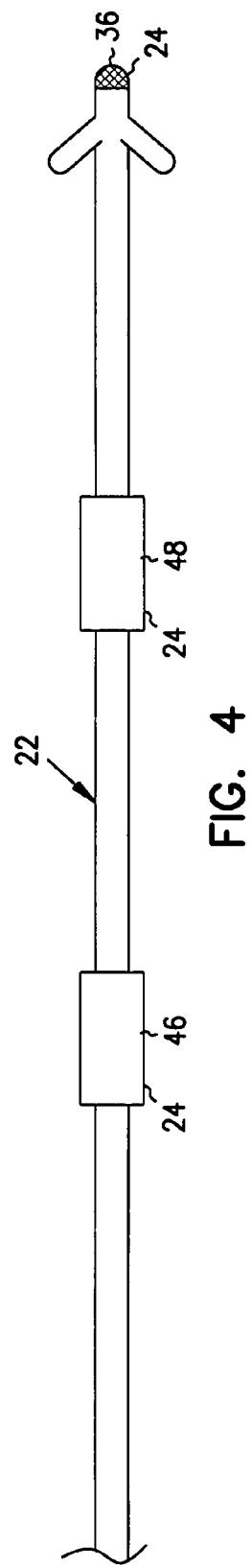

SYSTEM AND METHOD FOR GRAPHICALLY CONFIGURING LEADS

FIELD OF THE INVENTION

This invention relates generally to the field of medical devices, and more particularly to systems and methods for graphically representing configurations for medical devices.

BACKGROUND

Medical devices, including cardiac stimulus devices such as implantable cardiac pacemakers and implantable cardioverter defibrillators (ICDs), are surgically implanted within a patient and have one or more electrical leads that conduct signals to and receive signals from the patient's heart. Each electrical lead has at least one electrode. Electrode types include ring, tip, and coil electrodes. Tip electrodes are positioned at the tip of the lead, and ring electrodes are bands positioned along the length of the lead. Coil electrodes are exposed conductor coils positioned along the lead, and are often used as part of a defibrillator to disperse a strong signal throughout the heart. Several of these electrode types may be placed on a single lead, and several of these leads may be placed in or around an organ such as the heart. Additionally, each of the electrodes may be configured to transmit or conduct a signal or pulse, or to receive or sense a signal. As such, the lead(s) with the electrode(s) are in a configuration with respect to their position and their electrical character or nature. The electrical character of the electrode(s) may be changed, and one method for changing the configuration is through programming.

A programming device or programmer communicates with the device. One communication method uses a telemetry link that enables commands and data to be non-invasively transmitted and received between the programmer and the device. During a programming operation, a user sets programmable parameters, including those parameters that relate to the configuration of the electrode(s), to values that cause the medical device to work in an optimum way for a particular patient. There are a number of reasons for which it is desirable to change the configuration. One reason is that the appearance of an electrogram (ECG, EGM) and the detection of intrinsic heart signals can be improved by changing the sensing configuration for a particular patient. Another reason is that the anode usually drifts slightly over time in its threshold voltages and thus requires more power to deliver the same pacing pulse. Reprogramming or reconfiguring the pacemaker to switch over and pace from the cathode rather than the anode can reduce the power requirements. Yet another reason is that the pacing electrode may have been placed near or on top of a diaphragm nerve such that the patient hiccups at each pacing pulse. Changing the pacing pulse resolves this situation. The list of reasons given above are nonexclusive as one skilled in the art would recognize that other reasons exist.

As medical devices provide more leads, electrodes per lead, and programming parameters for the leads, programming a configuration tends to become more complicated and confusing. Due to discrepancies in the terminology and procedures used in the medical field between doctors, clinical engineers or other users, there may be problems in connecting a textual term such as "unipolar" or "bipolar" with the placement of the leads and the actual pacing and sensing vectors between the electrodes on the leads.

Therefore, there is a need in the art to provide a system and method for graphically configuring leads of medical devices.

SUMMARY OF THE INVENTION

The present subject matter provides systems and methods to address the aforementioned problems by graphically displaying configurations for medical devices. These systems and methods provide a programmer interface that graphically represents, illustrates or displays the lead(s), the electrode(s) on the lead(s), and the associated electrical vectors between the electrode(s) of the medical device. In a cardiac stimulation device such as a pacemaker or defibrillator, for example, the graphical representation may resemble the placement of leads inside and outside of the heart. Thus, the user visualizes the present configuration of the medical device through a graphical representation. In one embodiment, the graphical image illustrates how newly programmed settings would work before these changed settings are accepted and programmed into the medical device.

In one embodiment, the system generally comprises a medical device and a processing device, such as a programmer for example. The medical device has at least one lead, and each lead has at least one electrode. The lead(s) and electrode(s) are programmed, arranged or otherwise configured in an attempt to optimize the operation of the medical device for a particular patient. The programmer communicates with the medical device. The programmer provides a graphical display of the configuration for the medical device.

In one embodiment, the display includes an electrode representation and a lead representation. In other embodiments, the electrode representation includes but is not limited to one or more of the following representations: an electrode type representation, an electrode quantity representation, and an electrode position representation. Also, the lead representation includes but is not limited to a lead position representation for each lead. In an embodiment in which the medical device is a cardiac stimulus device such as a pacemaker or defibrillator, the lead representation includes a graphical representation or illustration of the arrangement of the lead(s) and the electrode(s) provided thereon as arranged within a heart. Further, in one embodiment, the graphical display represents a pulse polarity, an electrical vector between electrodes such as a pace vector, a sense vector, a defibrillation vector, or a vector for other types of energy delivery. Additionally, in one embodiment, the display includes a color scheme to distinguish the elements represented in the display.

Since a user is able to change the programmable parameters of medical devices, including those associated with configuring electrodes, one embodiment includes displaying both the current or present settings and the proposed or changed settings of the configuration. In one embodiment, the proposed or changed settings are entered by the user during the programming of the device, and the current or present settings are retrieved from a memory such as the memory of the programmer. A user reviews both settings to verify that the changed settings are desirable before accepting them.

The present subject matter provides a programmer device that generally comprises circuitry for communicating with a medical device having lead(s) with electrode(s) in a configuration, and a display for graphically representing the configuration. In one embodiment, the display of the programmer device includes both a lead representation and an electrode representation. In various embodiments, the lead representation includes a lead position representation; and the electrode representation includes one or more of the following representations: an electrode position representation, a pulse polarity representation, and an electrical vector representation.

The present subject matter also provides a computer-readable medium encoded with a software program for providing a graphical display of a lead configuration for an implantable medical device. In one embodiment, for example, this software program operates in a memory of a programmer for a medical device. In other embodiments, the software program operates in a memory of another processing device, such as a computer. The software program executes the following: receiving information about a lead configuration, and graphically representing the lead configuration. In other embodiments, graphically representing the configuration includes graphically displaying one or more of the following representations: a lead representation, an electrode representation, a pulse polarity representation, and an electrical vector representation. These representations graphically illustrate or display the physical lead configuration that includes, but is not limited to, one or more of the electrode quantity, the physical arrangement of the electrodes, the electrode type, the pulse polarity and the electrical vectors between the electrodes.

The present subject matter also provides a method that generally comprises: receiving information for a medical device having at least one lead with at least one electrode in a configuration, and presenting a graphical representation of the configuration. In one embodiment, the information is retrieved from a memory, such as that stored in a patient data section of the programmer. In another embodiment, presenting a graphical representation of the configuration information includes, but is not limited to, graphically representing one or more of the following: an arrangement of the lead(s) in a heart, an electrode type, a pulse polarity, an electrical vector between electrodes. In one embodiment, the method further comprises programming a change in the configuration. In one embodiment, presenting a graphical representation of the configuration information includes presenting both current settings and changed settings for the medical device.

These and other aspects, features, embodiments and advantages of the invention will become apparent from the following description of the preferred embodiments of the invention.

BRIEF DESCRIPTION OF THE DRAWINGS

FIG. 3 is an illustration of a lead having a tip electrode and coil electrodes.

FIG. 4 is an illustration of a lead having a tip electrode and ring electrodes.

DETAILED DESCRIPTION

In the following detailed description, references are made to the accompanying drawings that illustrate specific embodiments in which the invention may be practiced. Changes in the electrical, mechanical, structural, logical or programming designs may be made to the embodiments without departing from the spirit and scope of the present invention. The following detailed description is, therefore, not to be taken in a limiting sense and the scope of the present invention is defined by the appended claims and their equivalents.

The present subject matter addresses the aforementioned problems, and aspects of the present subject matter are shown and described herein. The present subject matter provides an interface for graphically displaying the configuration of medical devices. One embodiment graphically represents, illustrates or displays the lead(s), the electrode(s), the pulse polarity, and the electrical vectors associated with the configuration.

Various aspects of the present subject matter are presented below. One aspect is a system such as a cardiac rhythm management system. Another aspect is a processing device, such as a programmer or computer, found within the system. Other aspects include a software program that provides the graphical interface for viewing and changing the configuration, and a method of providing an interface for configuring a medical device. The software program is adapted to reside in the memory of a computer, such as a programmer, a personal computer or other processing device and to be executed by a processor.

Figure 1:
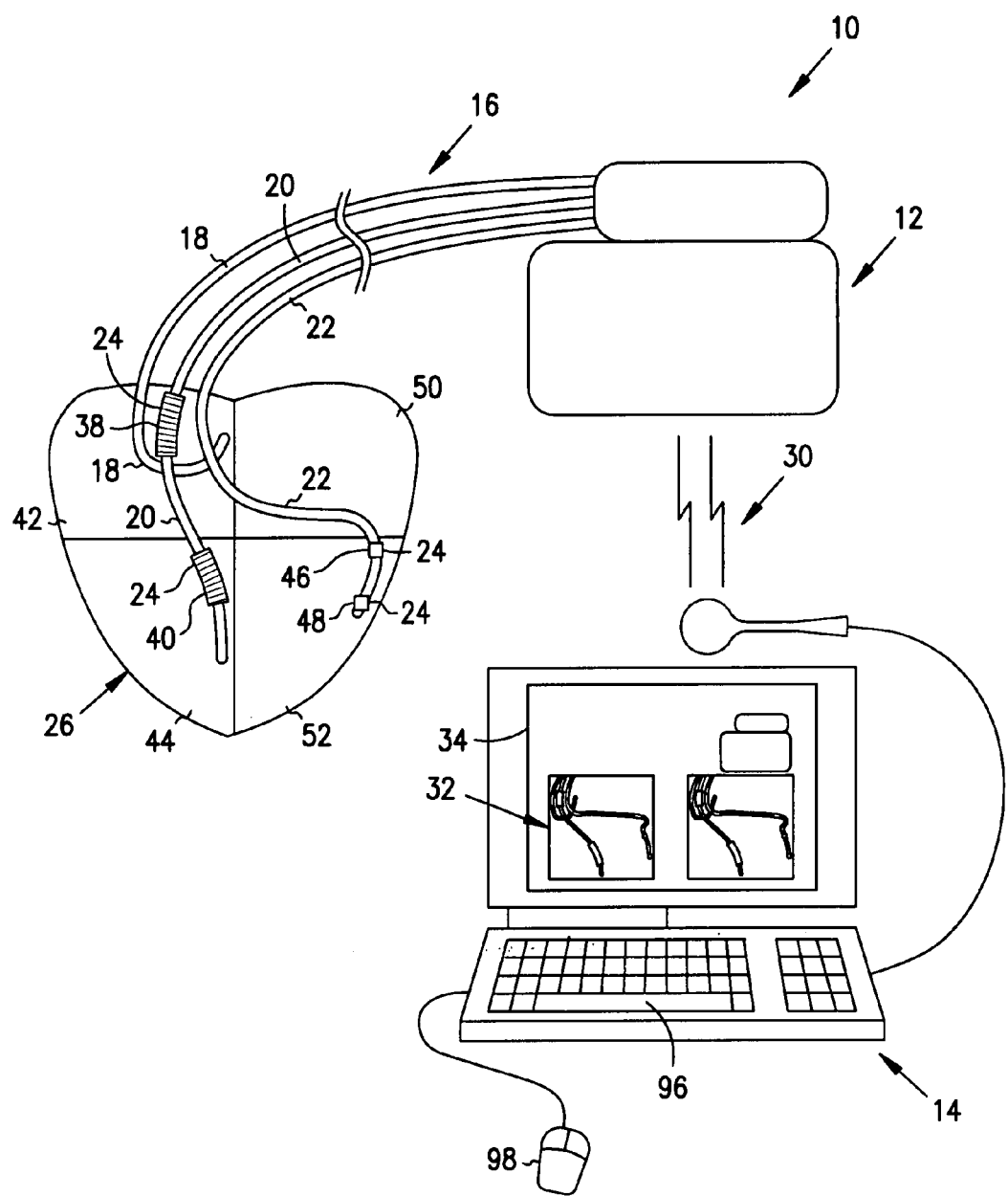
FIG. 1 is a schematic view of a system according to one embodiment.

FIG. 1 provides an illustration of a cardiac rhythm management system 10 according to the present subject matter. The system 10 generally comprises a medical device 12 and a programmer 14. The medical device 12 includes but is not limited to cardiac stimulation devices such as pacemakers and defibrillators. The medical device 12 has an electrode system 16 comprised of at least one lead and at least one electrode 24 for each lead. FIG. 1 shows an example in which there are three leads 18, 20 and 22. The leads 18, 20 and 22 are inserted into a patient's heart 26, and transmit electrical signals or pulses to the heart 26 and receive or sense electrical signals from the heart 26. The lead(s) 18, 20 and 22 and electrode(s) 24 are arranged, programmed and/or otherwise configured to provide the medical device 12 with a desired configuration in an attempt to optimize the operation of the medical device 12 for a particular patient.

The leads 18, 20 and 22 and the electrodes 24 on the leads are physically arranged with respect to the heart 26 in a fashion that enables the electrodes 24 to properly transmit pulses and sense signals from the heart 26. As there may be a number of leads 18, 20 and 22 and a number of electrodes 24 per lead, the configuration can be programmed to use a particular electrode or electrodes to provide the pulse and also to use particular electrodes to sense the electrical activity of the heart. As such, the lead configuration information for a medical device 12 includes but is not limited to one or more of the lead quantity, the physical arrangement of the leads 18, 20 and 22, the electrode quantity, the physical arrangement of the electrodes 24, the electrode type, the pulse polarity, and the electrical vectors between the electrodes.

Figure 2:
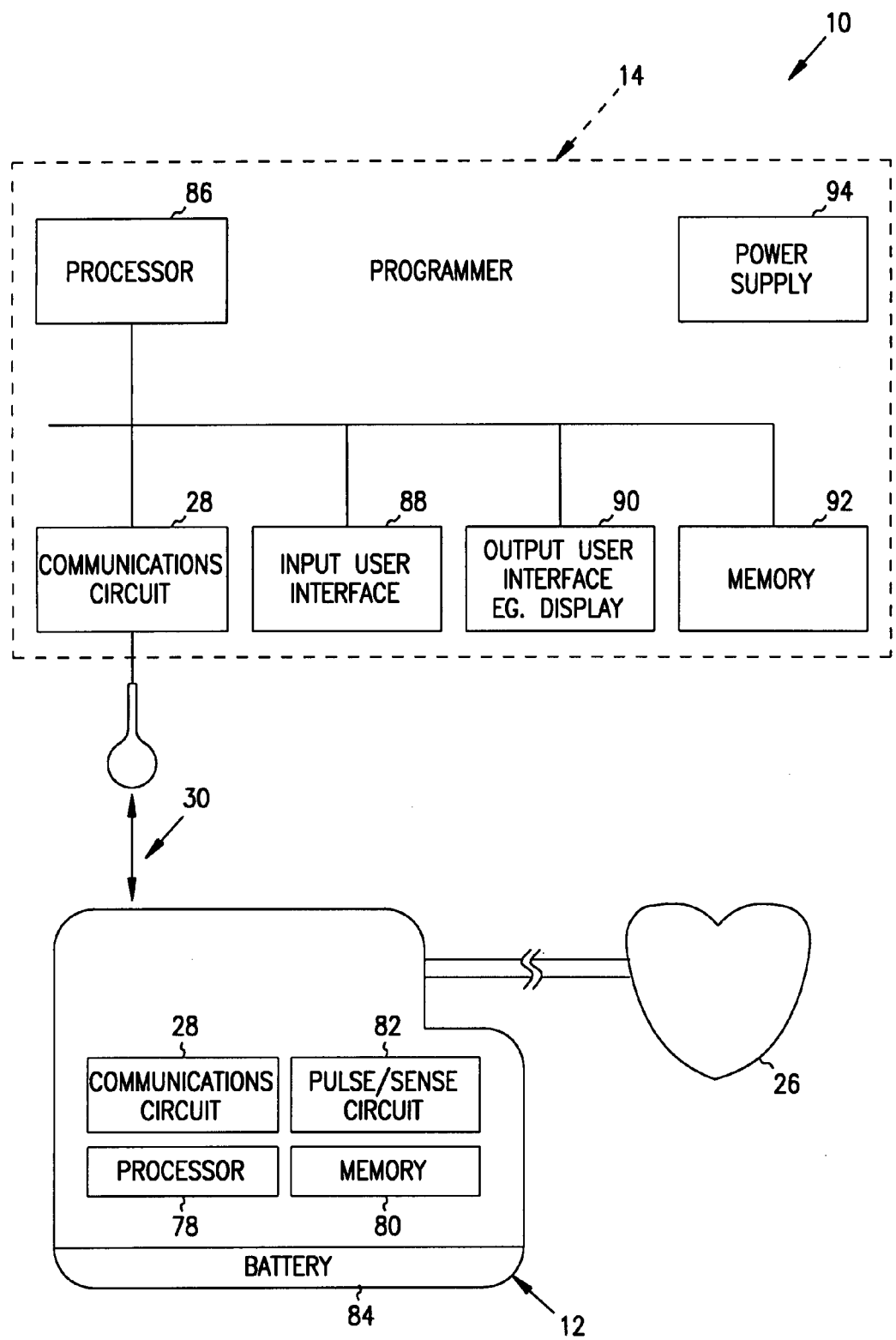
FIG. 2 is a block diagram of one embodiment of the system of FIG. 1.

FIGS. 1 and 2 show the processing device 14, such as a computer or programmer for example, coupled or otherwise in communication with the medical device 12. In one embodiment, the programmer 14 is coupled through complementary communication circuits 28 that provide a radio frequency telemetry channel 30 between the programmer 14 and the device 12. In another embodiment, the medical device 12 and programmer 14 communicate with each other using inductive coils. The programmer 14 has a graphical display 32 of the configuration for the medical device 12. In one embodiment, the graphical display 32 is a screen display 34 that forms an integral part of the programmer 14, computer or other processing device. However, the graphical display is not so limited. In one embodiment, the screen display 34 is an electronic display such as a CRT monitor that projects the image on a screen or a liquid crystal display LCD, for example. In other embodiments, the graphical display 32 includes other means for graphically displaying the configuration. These other means include, but are not limited to, printing out the graphical display 32 on a printer, and projecting the graphical display of the configuration on a device in communication with the programmer such as, for example, a local peripheral device, a remote device, or a device networked to the programmer. In one embodiment, a personal computer or other processing device, retrieves configuration information, defined above to include but not be limited to the quantity and physical arrangement of the leads 18, 20 and 22, the quantity and physical arrangement of the electrodes 24, the electrode type, the pulse polarity, and the electrical vectors between the electrodes. The computer then transmits the data remotely, over telecommunication lines, for example, to a clinic where it is displayed on a monitor or printed as the graphical display 32. One embodiment allows for communication over the Internet global computer network or world wide web. One embodiment of the processing device displays the graphical display 32 locally.

A physical illustration of a first lead 20 is provided in FIG. 3 and a physical illustration of a second lead 22 is provided in FIG. 4. Although not drawn to scale, these two illustrations are provided as examples of leads that correspond with the illustrated graphical displays 32 of FIGS. 5 and 6 discussed in more detail below. In no way should the inclusion of this example throughout this specification be read as limiting. The first lead 20 shown in FIG. 3 includes a tip electrode 36, a first coil electrode 38, and a second coil electrode 40. As generally shown in FIG. 1, this lead 20 may be inserted into the right atrium 42 and ventricle 44 so that the first coil electrode 38 is positioned in the right atrium 42 and the second coil electrode 40 is positioned in the right ventricle 44. The second lead 22 shown in FIG. 4 includes a tip electrode 36, a first ring electrode 46, and second ring electrode 48. Also as generally shown in FIG. 1, this second lead 22 may be inserted through the left atrium 50 and into the left ventricle 52 (coronary sinus implant) so that the first and second ring electrodes 46 and 48 are positioned in the left ventricle 52 and form a dual electrode configuration for the left ventricle 52.

Figure 5:
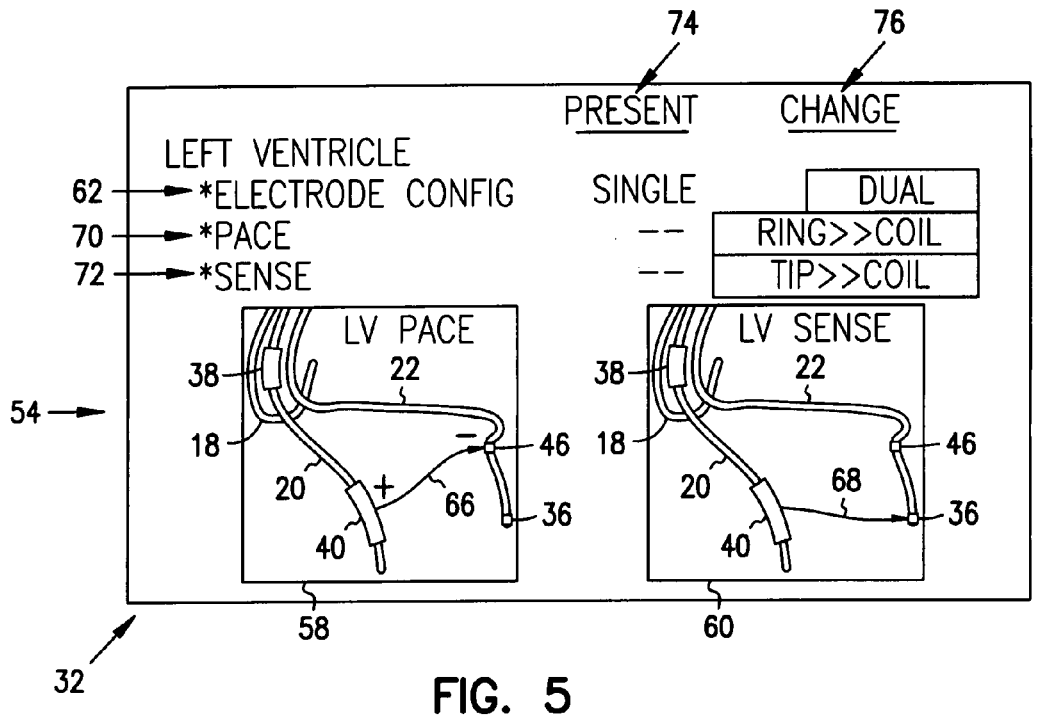
FIG. 5 is a first example of a graphical display illustrating a configuration for a medical device.
Figure 6:
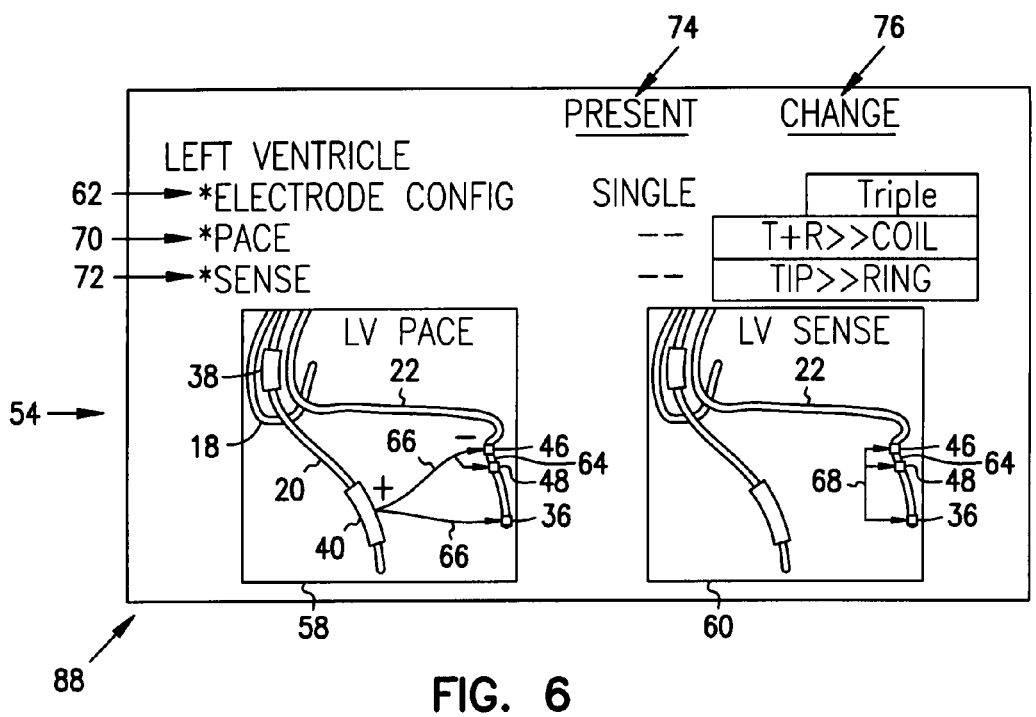
FIG. 6 is a second example of a graphical display illustrating a configuration for a medical device.

Graphical displays 32 for a first and second configuration 54 and 56 of a particular medical device 12 are illustrated in FIGS. 5 and 6. These displays 32 illustrate the leads 20 and 22 that are shown in FIGS. 3 and 4 and that are generally positioned as illustrated in FIG. 1. Each image 58 and 60 in the illustrated graphical display 32 contains three lines, wherein each line provides a lead representation. The first line represents the first lead 20 of FIG. 3 extending through the right atrium 42 and ventricle 44 as described above and as generally illustrated in FIG. 1. The second line represents the second lead 22 of FIG. 4 extending into the left ventricle 52 as illustrated in FIG. 1. A third line represents an atrial lead 18 extending into the right atrium 42 as illustrated in FIG. 1. These figures illustrate one example of a configuration. Other leads or lead positions are displayed for other specific configurations of a medical device 12. In the illustrated embodiment, an electrode representation is provided by the bands 38 and 40 on the first lead 20 and the dots 36 and 46 on the second lead 22. The bands 38 and 40, represented by thicker lines in these monochromatic figures, represent coil electrodes 38 and 40 and their respective positions on the first lead 20, and the dots represent tip and ring electrodes 36 and 46 and their respective positions on the second lead 22.

Additionally, in one embodiment, a color scheme is used to distinguish or otherwise represent the elements contained in the display. For example, in one embodiment, the leads are represented by colored lines such as blue for the right atrium lead 18, purple for the right ventricle lead 20, and orange for the left ventricle lead 22. Additionally, the coil electrodes 38 and 40 are represented as black bands on the purple lead 20, and the tip and ring electrodes 36 and 46 are represented as black dots on the orange second lead 22. Although the exact color scheme used may vary, the use of the color scheme to distinguish the elements contained in the display enhances the ability of the graphical display 32 to quickly and easily convey information as part of the interface of the programmer 14. In one embodiment, the bands 38 and 40 may be represented by a color distinction, such as black on a colored lead line, rather than by a thicker line. Further, in one embodiment, selected elements in the display are represented as blinking elements.

As is understood from FIGS. 5 and 6, the lead representation includes but is not limited to a lead position or arrangement representation for each lead 18, 20 and 22. That is, the graphical display 32 provides an indication or representation of how the leads 18, 20 and 22 are arranged in the patient. And for a cardiac stimulus device such as a pacemaker or a defibrillator, the lead representation may include a graphical representation of the arrangement of the lead(s) 18, 20 and 22 and electrode(s) 24 as they are positioned within a heart 26. This is shown by comparing the arrangement of the graphically illustrated leads 18, 20 and 22 shown in the displays of FIGS. 5 and 6 with the physical arrangement of the leads 18, 20 and 22 in the heart 26 of FIG. 1 and the physical illustration of the leads themselves in FIGS. 3 and 4. The arrangement of the illustrated leads 18, 20 and 22 corresponds to the arrangement of the physical leads 18, 20 and 22 in the heart 26. The accuracy in correlating the physical position or arrangement of the leads with a lead position representation varies among embodiments. In one embodiment, for example, any lead that is inserted in or around the left ventricle may be represented by the lead 22 that is illustrated in FIG. 5. Another embodiment provides a closer correlation between the actual physical arrangement of the lead and the lead position representation such that the lead 22 illustrated in FIG. 5 only represents a physical lead that has been positioned into a mid-lateral position of the left ventricle, and another lead, that is not illustrated, represents a physical lead positioned elsewhere in or around the left ventricle.

Also, as is understood from FIGS. 5 and 6, this particular embodiment of the electrode representation provides an electrode quantity representation for each lead 18, 20 and 22, an electrode position representation for each electrode 24, and an electrode type representation for each electrode 24.

With respect to the electrode quantity representation, FIG. 5 shows that the medical device 12 has a total of four electrodes 38, 40, 46 and 36 with two on the first lead 20 and two on the second lead 22, and FIG. 6 shows that the medical device has a total of five electrodes 38, 40, 46, 48 and 36 with two on the first lead 20 and three on the second lead 22.

With respect to the electrode position representation, FIG. 5 shows that the first lead 20 has an electrode 38 in the right atrium 42 and another electrode 40 in the right ventricle 44, and that the second lead 22 has an electrode 36 on its distal end and another electrode 46 along its length that, as illustrated, together form a dual electrode configuration for the left ventricle 52. This dual electrode configuration also is provided in the *Electrode Config row 62 of the table at the top of FIG. 5. Similarly, it is seen in FIG. 6 that the first lead 20 has an electrode 38 in the right atrium 42 and another electrode 40 in the right ventricle 44, and that the second lead 22 has an electrode 36 on its distal end and two other electrodes 46 and 48 along its length that, as illustrated, together form a triple electrode configuration for the left ventricle 52. This triple electrode configuration also is provided in the *Electrode Config row 62 of the table at the top of FIG. 6. The accuracy in correlating the physical position of the electrodes with an electrode representation varies among embodiments.

With respect to the electrode type representation, FIG. 5 shows that the two electrodes illustrated by the two bands 38 and 40 on the first lead 20 indicate that those electrodes are coils, that the electrode illustrated by the dot 36 at the distal end of the second lead 22 is a tip electrode, and that the electrode illustrated by the other dot 46 along the length of the second lead is a ring electrode. FIG. 6 shows that the two electrodes illustrated by the two bands 38 and 40 on the first lead 20 indicate that those electrodes are coils, that the electrode illustrated by the dot 36 at the distal end of the second lead is a tip electrode, and that the two electrodes illustrated by the other two dots 46 and 48 along the length of the second lead 22 are ring electrodes. It is further noted that, as indicated by the line connecting these other two dots, these two ring electrodes 46 and 48 are electrically connected to form one electrode. In one embodiment, a color scheme is used to represent an electrode type either in addition to or in place of using shapes and electrode positions to determine the electrode type.

One embodiment of an electrode representation is provided by the above-described electrode quantity representation, electrode position representation, and electrode type representation for each electrode. The electrode representation is not so limited to the particulars of that embodiment, however. Other embodiments use other images and icons to represent electrode quantity, electrode position, lead position, and electrode type.

Further, as is understood from FIGS. 5 and 6, the graphical display 32 may represent electrical vectors between electrodes, such as the illustrated pace vectors 66 and sense vectors 68, and a pace polarity. First, each of the illustrated screen displays includes two illustrations 58 and 60. The first illustration provides a pace vector illustration 58, and the second illustration provides a sense vector illustration 60. Specifically, for the examples of the graphical displays 32 shown in FIGS. 5 and 6, the pace and sense vector illustrations 58 and 60 are for the left ventricle 52.

The vector representations are not limited to the illustrated pace vectors 66 and sense vectors 68, but rather include vectors for other types of energy delivery such as defibrillation vectors. One example of a defibrillation vector is "Distal Spring to Proximal Spring", i.e. distal coil electrode 40 to proximal coil electrode 38. Another example of a defibrillation vector is "Distal Spring to Can (PG)", in which the medical device 12 is referred to as a pulse generator, i.e. PG, or can. In this example, the can forms one of the electrodes and the distal coil electrode 40 forms the other electrode for the defibrillation vector. A simplified bradycardia device, for example, also paces from the distal electrode back to the can.

Referring now to the LV Pace illustration 58 of FIG. 5, a pace vector 66 indicates that the pace pulse is being transmitted between the coil 40 in the right ventricle 44 and the ring electrode 46 in the left ventricle 52, and the polarity of the pace pulse is represented by the plus (+) and minus (−) signs next to the vector 66. Therefore, the pace configuration is said to be "Ring-to-Coil" as indicated in the "*Pace" row 70 of the table on the top of FIG. 5, which means that the Ring electrode 46 paces against the coil electrode 40. Similarly, referring now to the LV Pace illustration of FIG. 6, a pace vector 66 indicates that the pace pulse is being transmitted between the coil 40 in the right ventricle 44 and the ring electrodes 46 and 48 and tip electrode 36 in the left ventricle 52. The polarity of the pace pulse, as represented by the plus (+) and minus (−) signs next to the vector, indicates that the pace configuration is "T+R to Coil", as provided in the "*Pace" row 70, which means that the Tip 36 and Ring 46 and 48 together pace against the Coil 40.

Referring now to the LV Sense illustration 60 of FIG. 5, a sense vector 68 indicates that electrical signals from the heart 26 are being detected between the coil 40 in the right ventricle 44 and the tip electrode 36 in the left ventricle 52. Therefore, the sense configuration is said to be "Tip to Coil" as provided in the "*Sense" row 72 of the table on the top of FIG. 5. Similarly, referring now to the LVSense illustration 60 of FIG. 6, a sense vector 68 indicates that electrical signals from the heart 26 are being detected between the tip 36 and the two ring conductors 46 and 48. Therefore, the sense configuration is said to be "Tip to Ring" as provided in the "*Sense" row 72.

One embodiment has been described above for the pace polarity representation (i.e. the plus and minus signs), the pace vector representation 58, and the sense vector representation 60. The representations are not so limited to the particulars of that embodiment, however. Other embodiments use other images and icons to represent pace polarity, and vector(s).

In one embodiment, the programmer 14 is used to change the programmable parameters of the medical device 12, including those parameters for configuring the electrode(s) of the medical device 12. As such, the programmer 14 provides means for changing a configuration, and a user of the programmer performs the step of programming a change in the configuration. In one embodiment, the graphical display 32 represents the current or present settings 74 of the configuration which were previously stored in a memory such as the memory of the programmer 14. And in another embodiment, the graphical display 32 represents the changed or proposed changed settings 76. Thus a user can review both settings to verify that the changed settings 76 are desirable before accepting them.

FIG. 2 illustrates a block diagram of the system shown in FIG. 1. In one embodiment, the medical device 12 is a programmable microprocessor-based system that generally comprises a processor 78, a memory 80, a communication circuit 28, pulse/sense circuitry 82, and a power supply or battery 84. The processor 78 and memory 80 are used to control the process steps conducted by the medical device 12. For example, the processor 78 is programmed to detect a sensed condition or response in a patient's heart 26 and to respond appropriately. The memory 80 contains parameters for various pacing and sensing modes, and further stores data concerning the condition of the heart 26 as derived from the received cardiac signals. The medical device 12 uses the pulse/sense circuitry 82 to interface with the leads, i.e. to transmit the signal to the heart 26 and to receive the signal from the heart 26 through these leads. The communication circuit 28 allows the medical device 12 and the programmer 14 to communicate with each other.

Another aspect of the present subject matter provides a device 14, such as a programmer, personal computer or other processing device, which is also shown in the block diagram of FIG. 2. The processing device 14 generally comprises a processor 86, a circuit 28 for communicating with a medical device 12, an input user interface 88, an output user interface 90, memory 92 and a power supply 94. The circuit 28 for communicating with a medical device comprises inductive coils in one embodiment and telemetry circuitry radio frequency telemetry circuitry in another embodiment. The input user interface 88 includes, but is not limited to, a keyboard 96, a mouse 98, a light pen and a touch screen. Further, in one embodiment, the output user interface 90 includes, but is not limited to, printers and displays. In one embodiment, the graphical display 32 is an electronic display such as a CRT monitor or LCD, for example, that forms an integral part of the programmer 14. However, the graphical display 32 is not so limited. In other embodiments, the graphical display includes other means for graphically displaying the configuration. These other means include, but are not limited to, printing out the graphical display of the configuration on a printer, and projecting the graphical display of the configuration on a device in communication with the programmer 14 such as, for example, a local peripheral device, a remote device, or a device networked to the programmer 14.

FIGS. 5 and 6 show that one embodiment of the graphical display 32 of the programmer device 14 includes both a lead representation 18, 20 and 22 and an electrode representation 36, 38, 40, 46 and 48. In one embodiment, the lead representation includes a lead position representation. The graphical display 32 has been shown and described above with respect to the system aspect 10 of the present invention and as such will not be reiterated here with respect to the programmer device 14.

Figure 7:
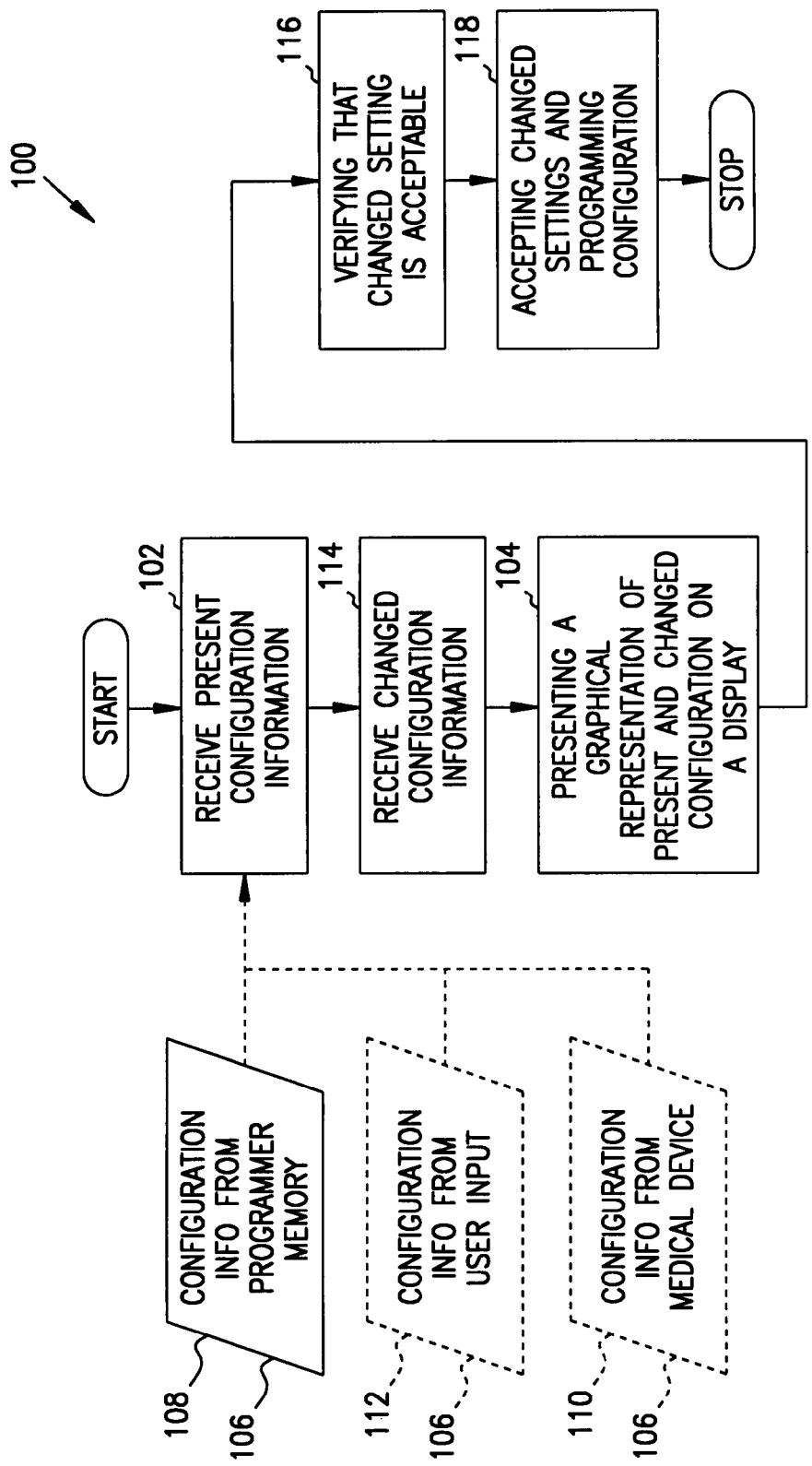
FIG. 7 is a flow diagram for a software program according to one embodiment.

FIG. 7 provides a flow chart for a software program 100 that provides a programming interface for an implantable medical device 12. The software program 100 is encoded in a computer-readable medium, i.e. the memory 92 of the programmer 14, computer or other processor device for example. The illustrated software program 100 generally executes the following: at 102, receiving information about a configuration; and at 104, graphically displaying the configuration. As provided above, the lead configuration information for a medical device 12 includes but is not limited to the quantity and physical arrangement of the leads 18, 20 and 22, the quantity and physical arrangement of the electrodes 24, the electrode type, the pulse polarity, and the electrical vectors between the electrodes.

Receiving information about a configuration requires a data input 106 for the configuration information. One embodiment of this step is illustrated at 108. The programmer 14 has a memory 92 that contains a "patient data" section. One means for receiving information about a configuration is to store this information in the programmer memory 92 as part of the patient data, and then selectively retrieve that information from the programmer memory 92. Thus, during the implant of the medical device, the doctor, clinical engineer or other user will enter lead identification and pacing site information for the implanted leads into the memory 92 of the programmer 14. Alternatively, at 110, this information is stored in the memory 80 of the medical device 12 and retrieved by any doctor or clinical engineer at any location using another programmer. The relevant information travels with the patient without being limited by the location of the patient's doctor or clinic, and the clinic's programmer. Another alternative is shown at 112; namely that this information may be provided from a user who has reviewed the medical history of the patient. Although not shown in the figures, other means for inputting this information include magnetic and optical scanners, whereby the information is appropriately encoded into a card or other medium that is capable of being magnetically or optically scanned, or otherwise read.

In one embodiment, when the software program graphically displays the configuration at 104, the software program is graphically displaying one or more of the following representations: a lead representation, an electrode representation, a pulse polarity, and a vector. The display and the representations incorporated therein have been discussed above with respect to the system 10 and as such will not be reiterated here with respect to the software program. In other embodiments, the software program executes the following: at 114, receiving changed configuration information, such as through a user input when a user is programming the configuration; at 116, verifying that the changed setting is acceptable; and at 118, upon verifying that the changed settings are acceptable, accepting the changed settings and programming the configuration.

Figure 8:
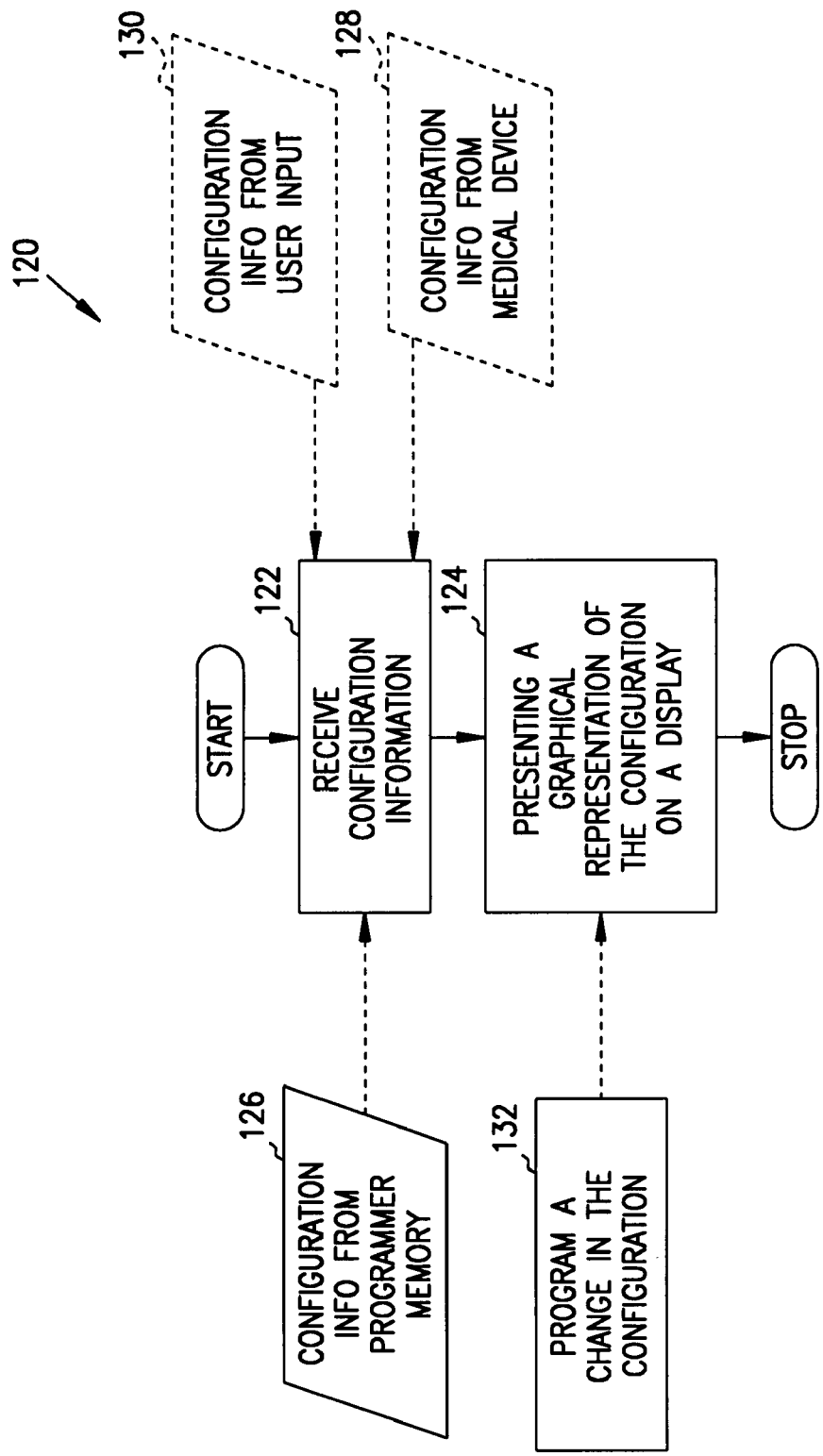
FIG. 8 is a flow diagram for a method according to one embodiment.

FIG. 8 provides a flow chart for a method aspect 120 of the present subject matter. The method 120 generally comprises the steps of: at 122, receiving configuration information for a medical device having at least one lead with at least one electrode; and at 124, presenting a graphical representation of the configuration information on a display. In one embodiment, at 126, the configuration information is retrieved from a memory, such as that stored in a patient data section of the programmer. Alternatively, at 128, this information is stored in the memory of the medical device and retrieved by any doctor or clinical engineer at any location using another programmer. Another alternative is that, at 130, this information is provided from a user who has reviewed the medical history of the patient.

In another embodiment, the method further comprises at 132, programming a change in the configuration. As described above, this step is performed by a user who is using a programmer to program or otherwise configure the medical device. In this embodiment, presenting a graphical representation of the configuration includes presenting both current settings and changed settings for the medical device. A user reviews both the current and changed settings to determine whether the changes should be programmed into the medical device.

In another embodiment, the step of presenting a graphical representation of the configuration information may include, but is not limited to, presenting one or more of the following graphical representations: an arrangement of the lead(s) in a heart, an electrode type, a pulse polarity, and vectors.

A graphical display of the configuration has been discussed above in detail with respect to the system aspect of the present invention and as such will not be reiterated here with respect to the method aspect of the present invention.

FIGS. 9–27 illustrate vectors for a lead configuration of a medical device. The particular lead configuration, including the position of the leads, and the vectors or illustrated as examples of vectors, and do not provide an exclusive list of available configurations.

Figure 9:
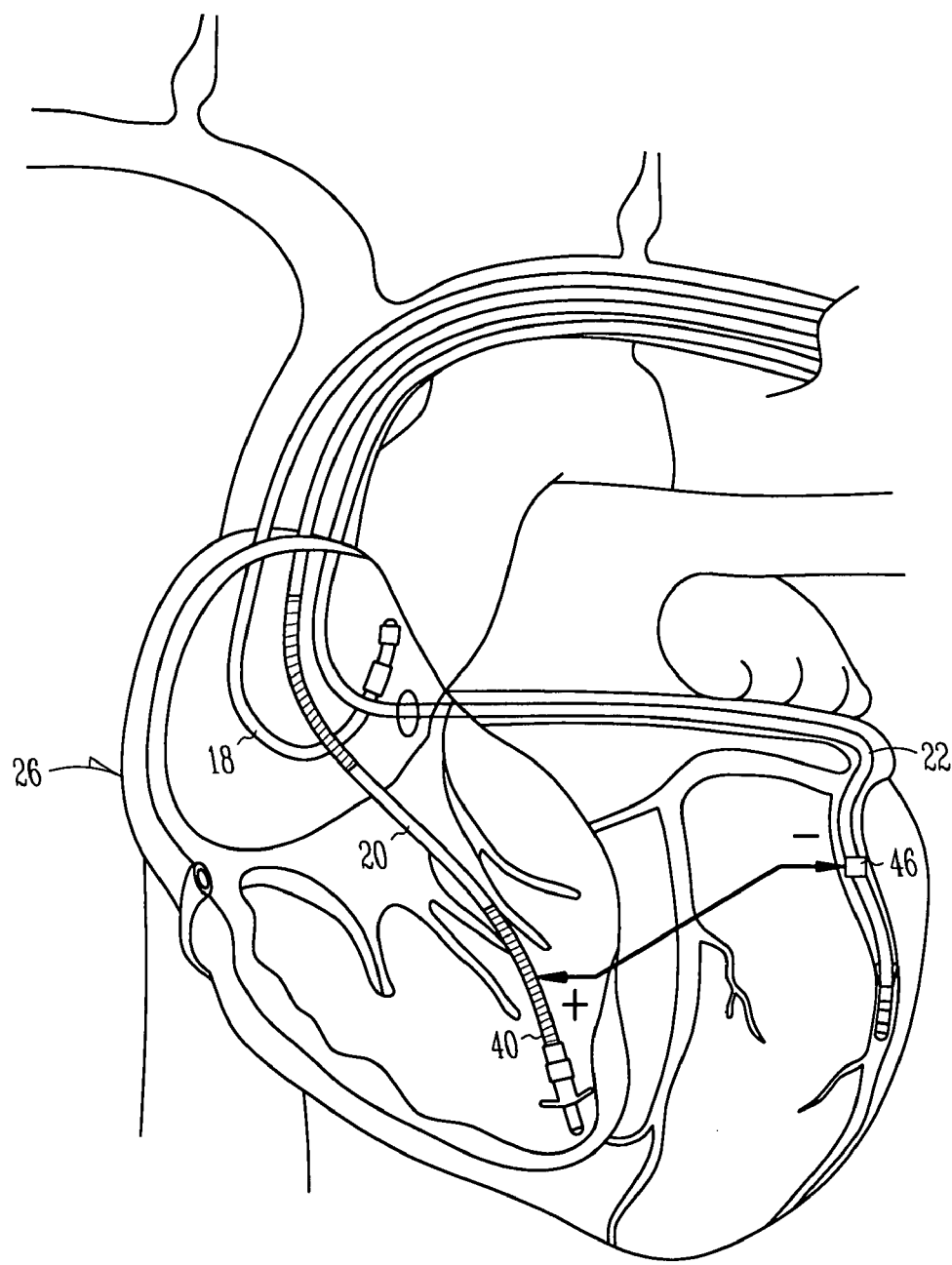
FIGS. 9–14 illustrate pacing vector examples for a left ventricular lead.
Figure 10:
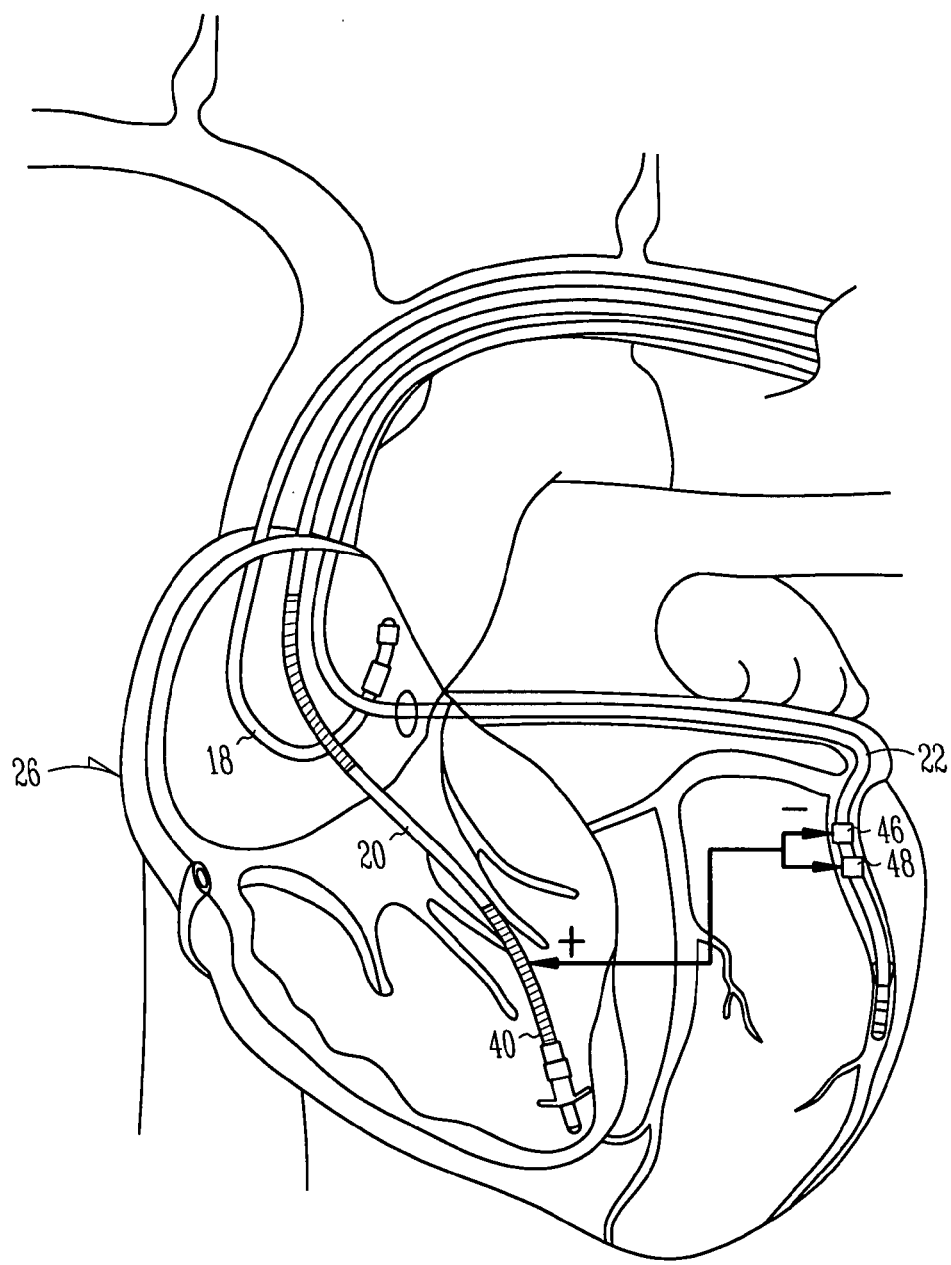
Figure 11:
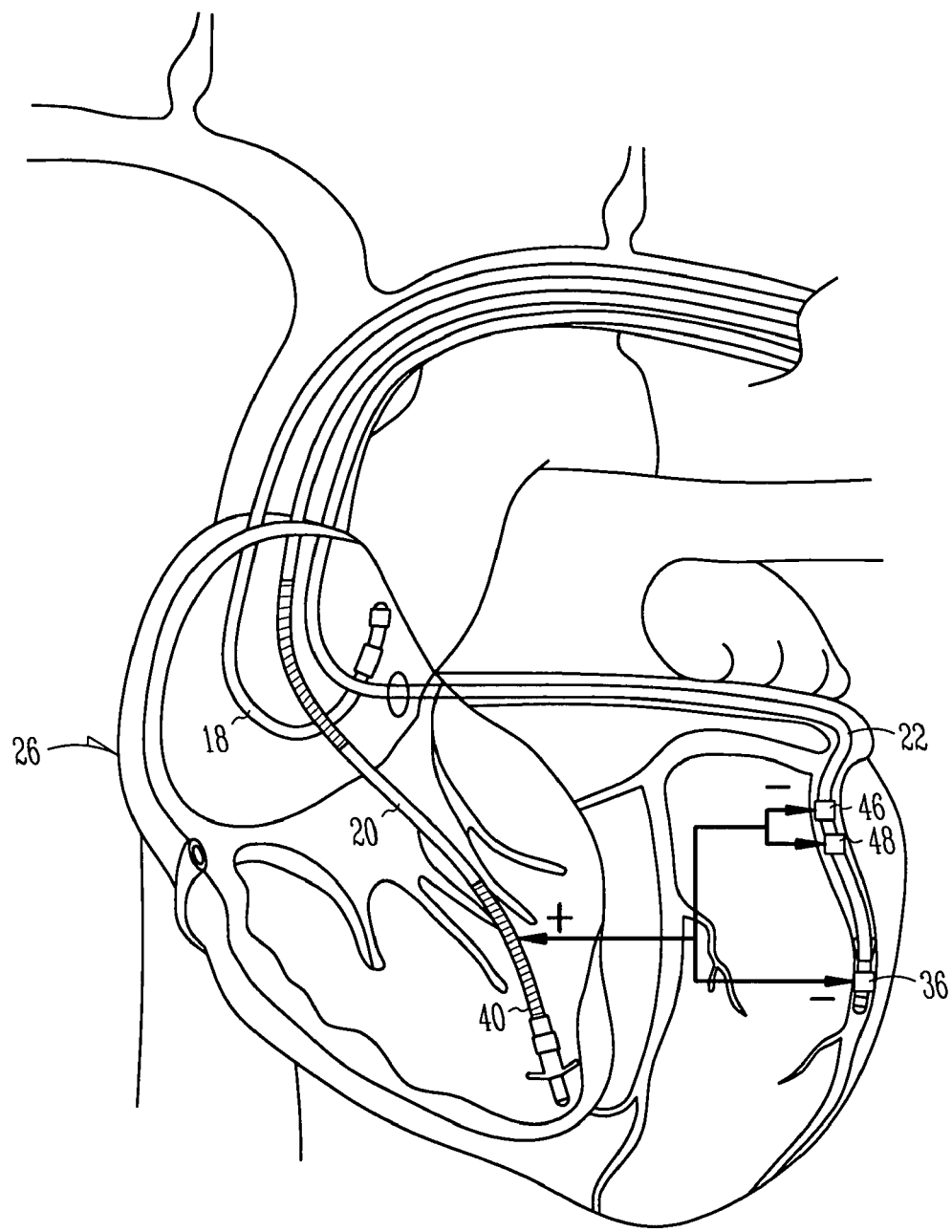
Figure 12:
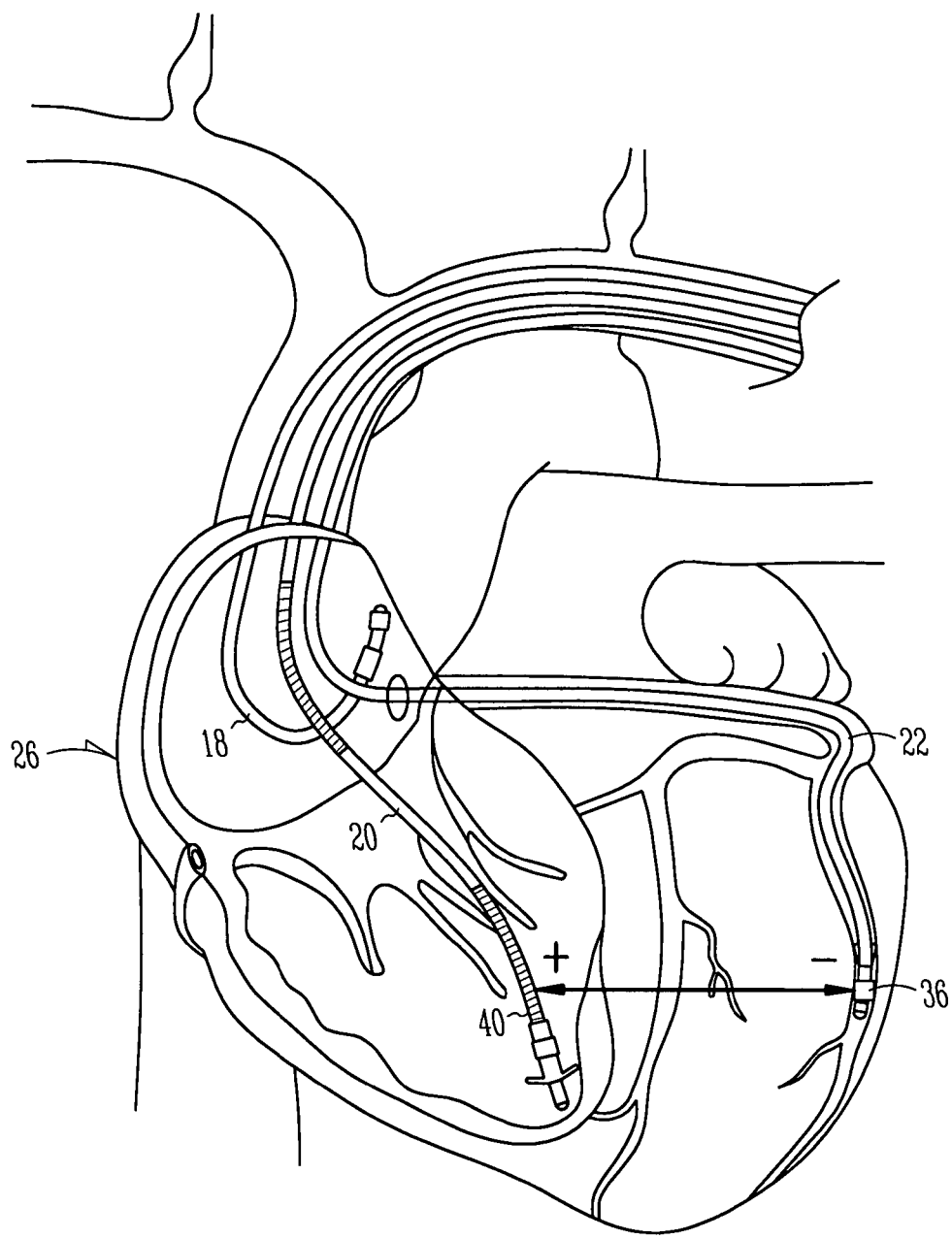
Figure 13:
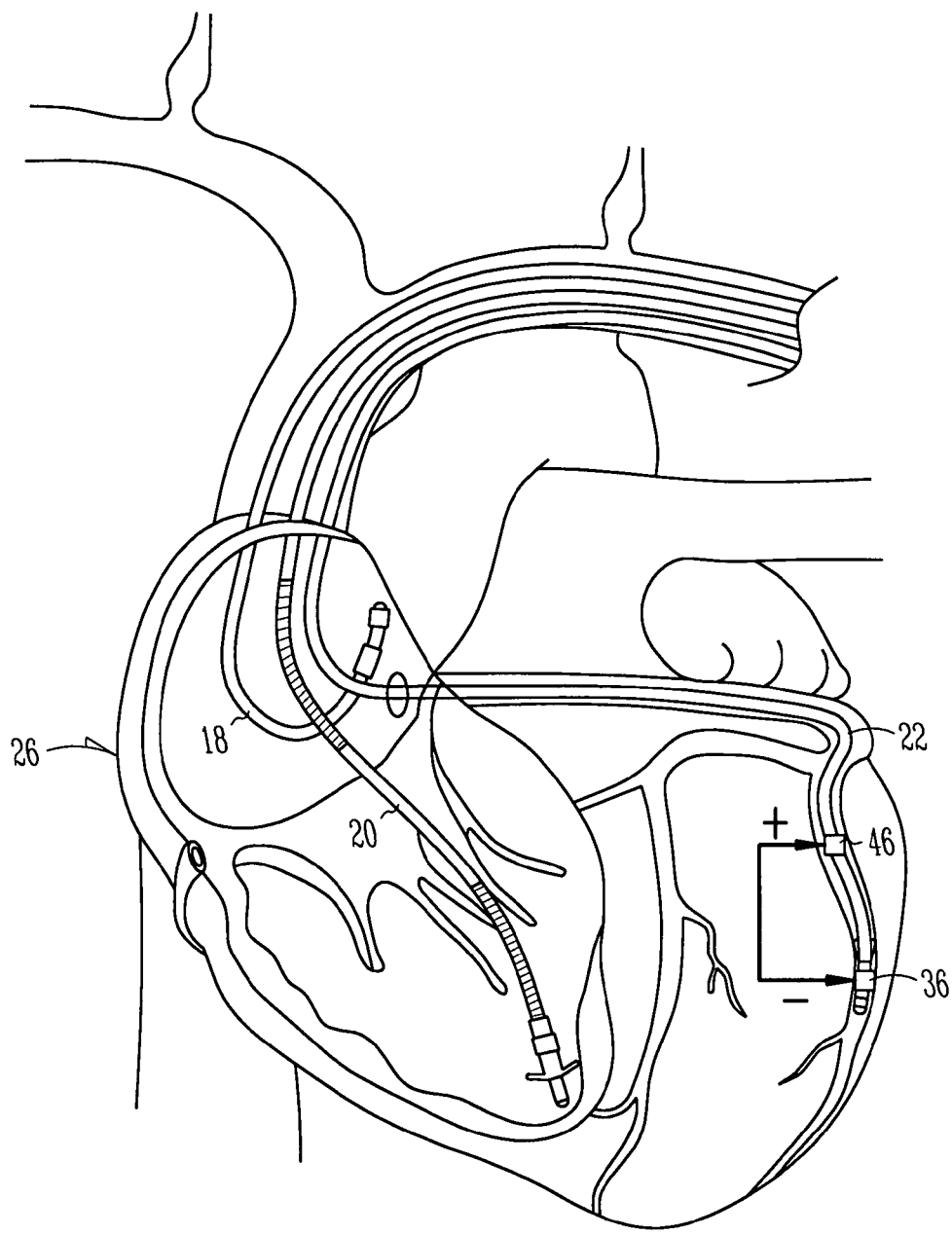
Figure 14:
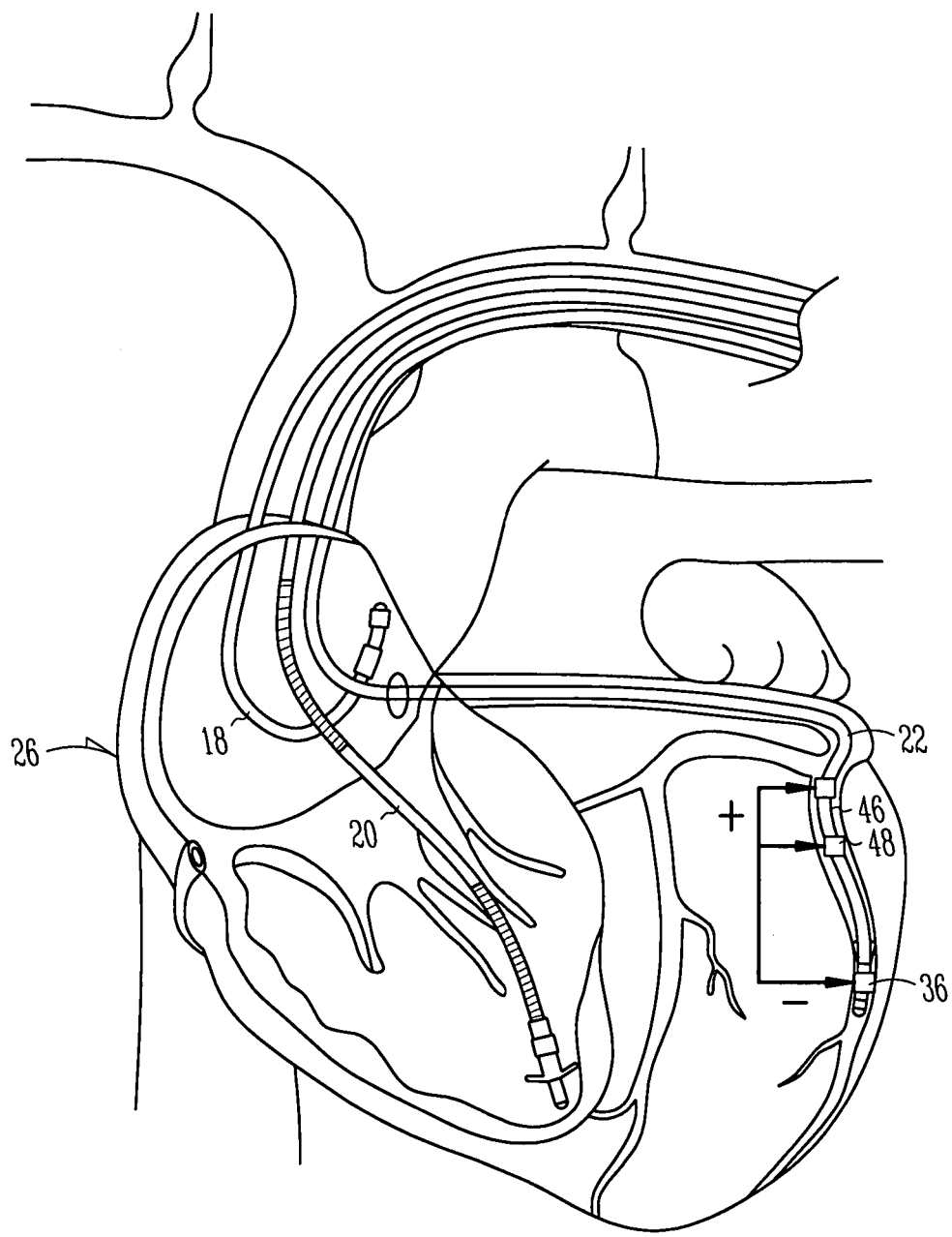

FIGS. 9–14 illustrate pacing vector examples for a left ventricular lead. FIG. 9 shows a left ventricular pace from a ring electrode 46 positioned on a left ventricular lead 22 to a coil electrode 40 positioned on a right ventricular lead 20. FIG. 10 shows a left ventricular pace from two ring electrodes 46 and 48 positioned on a left ventricular lead 22 to a coil electrode 40 positioned on a right ventricular lead 20. FIG. 11 shows a left ventricular pace from two ring electrodes 46 and 48 and a tip electrode 36 positioned on a left ventricular lead 22 to a coil electrode 40 positioned on a right ventricular lead 20. FIG. 12 shows a left ventricular pace from a tip electrode 36 positioned on a left ventricular lead 22 to a coil electrode 40 positioned on a right ventricular lead 20. FIG. 13 shows a left ventricular pace from a tip electrode 36 to a ring electrode 46, both of which are positioned on a left ventricular lead 22. FIG. 14 shows a left ventricular pace from a tip electrode 36 to two ring electrodes 46 and 48, all of which are positioned on a left ventricular lead 22.

Figure 15:
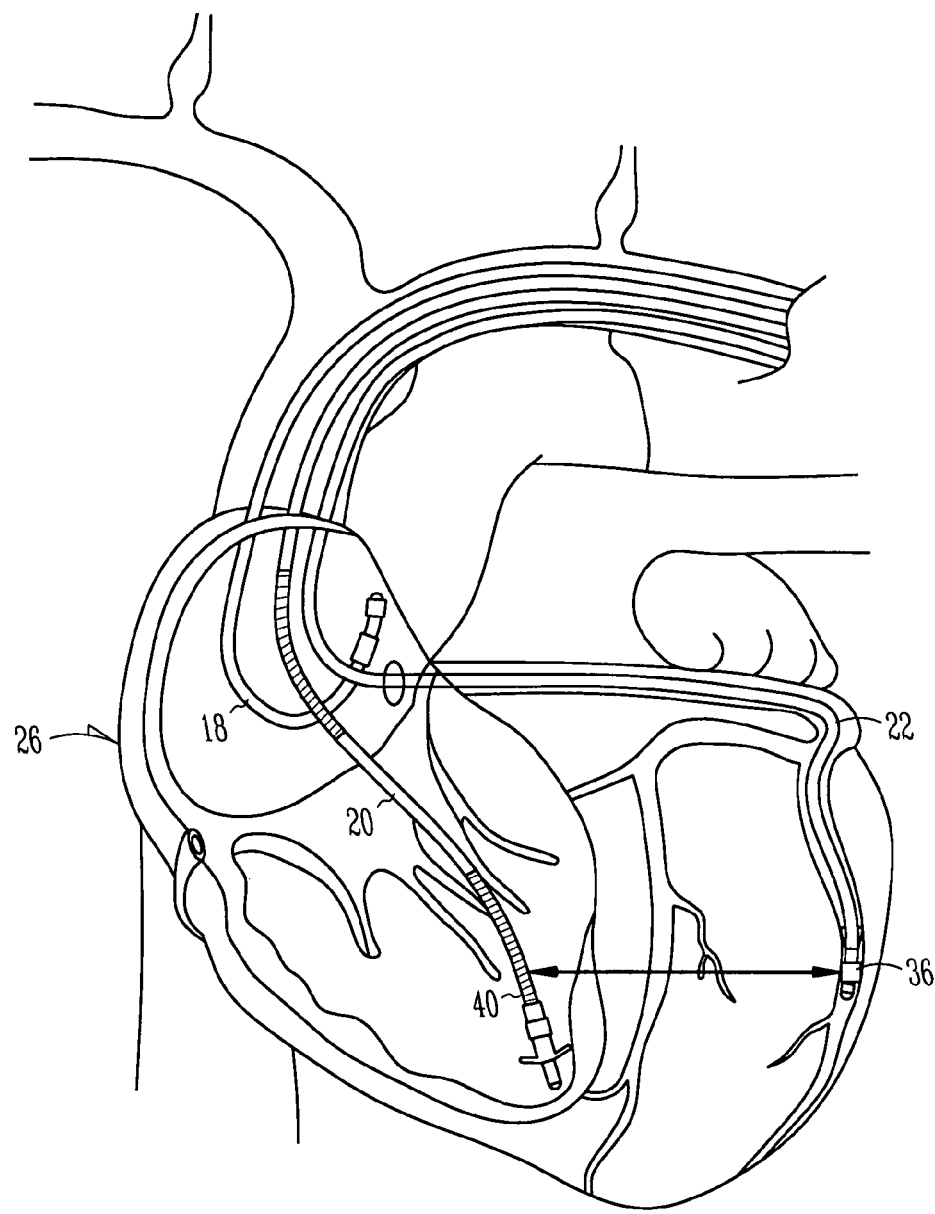
FIGS. 15–17 illustrate sensing vector examples for a left ventricular lead.
Figure 16:
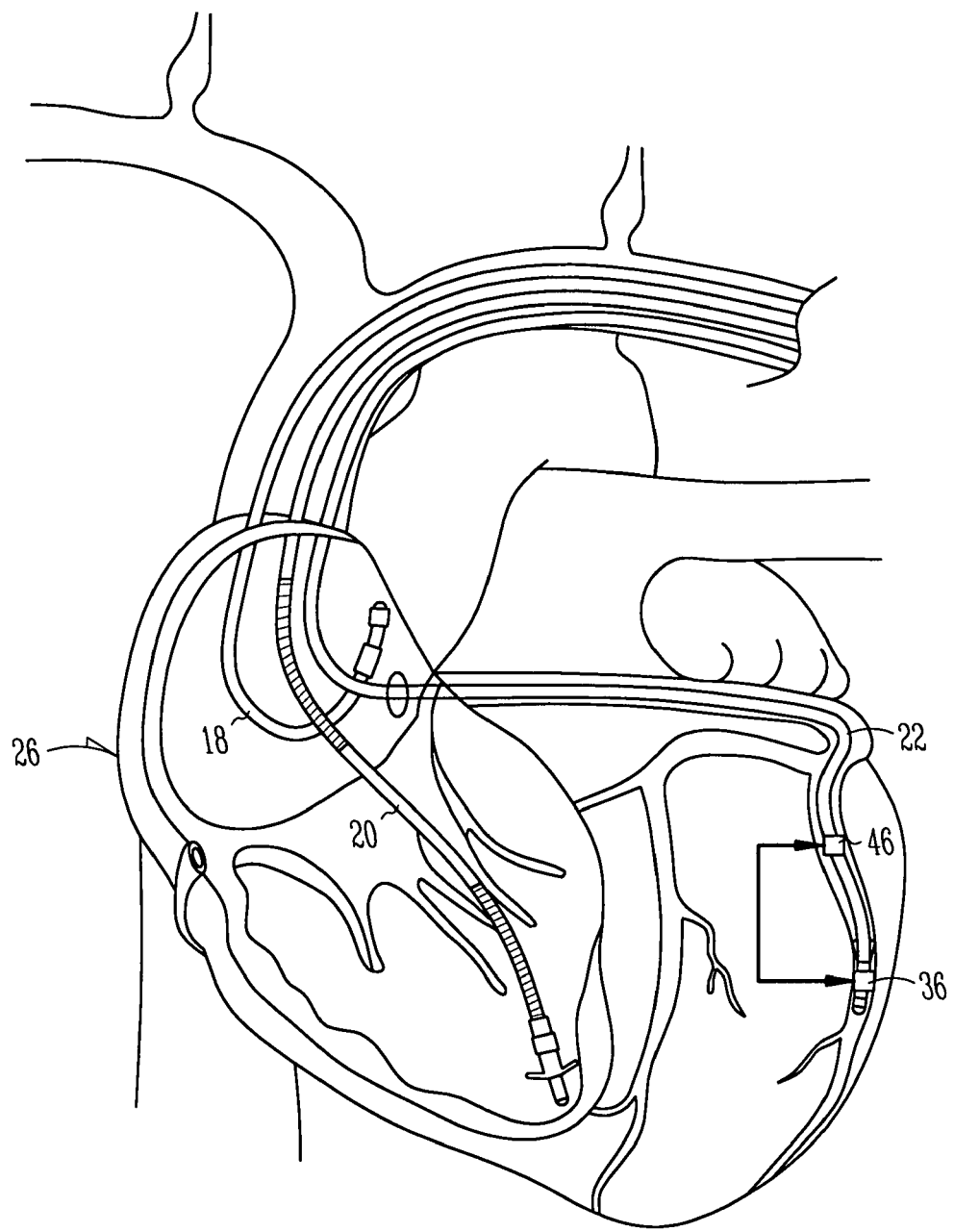
Figure 17:
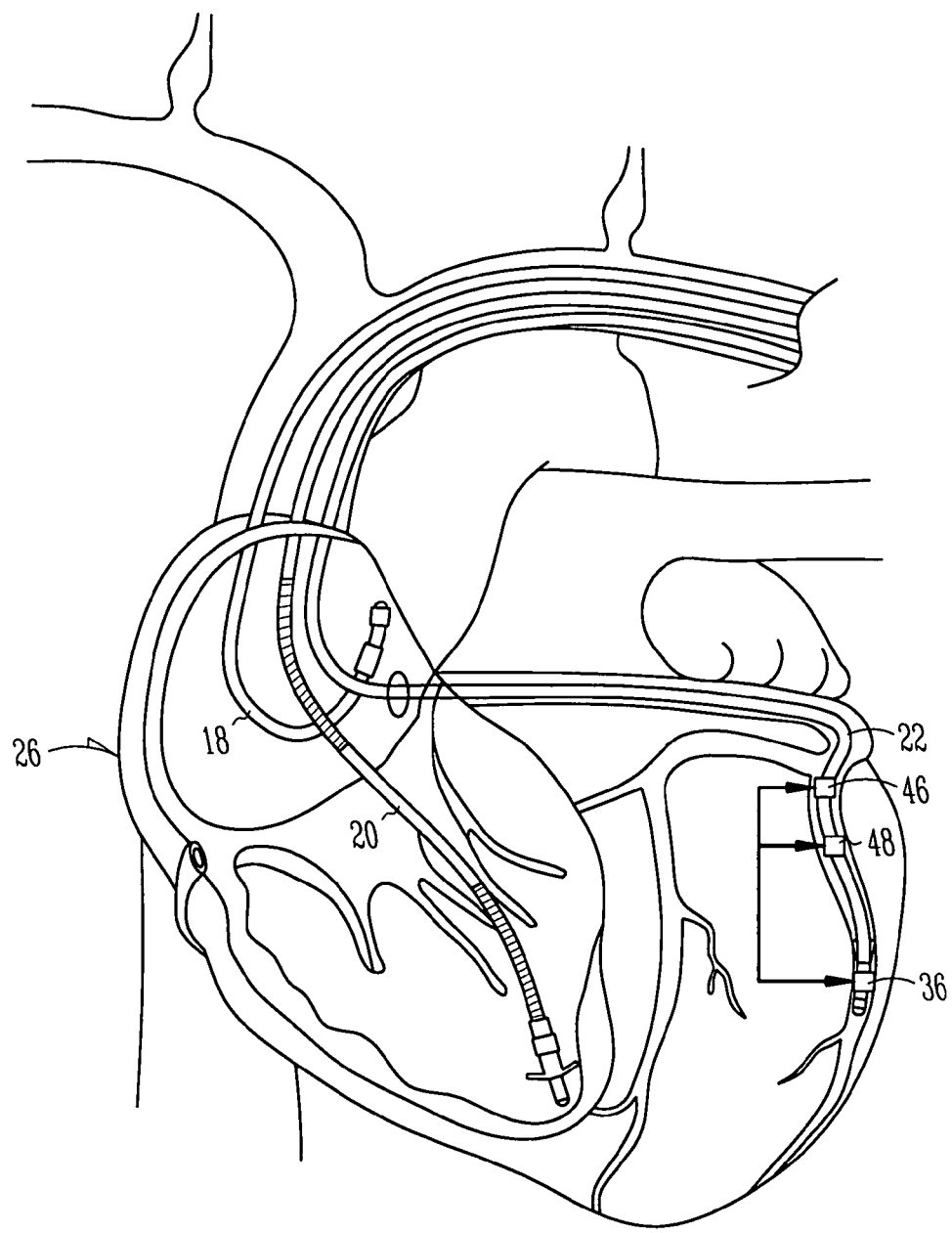

FIGS. 15–17 illustrate sensing vector examples for a left ventricular lead. FIG. 15 shows a left ventricular sense between a tip electrode 36 positioned on a left ventricular lead 22 and a coil electrode 40 positioned on a right ventricular lead 20. FIG. 16 shows a left ventricular sense between a tip electrode 36 a ring electrode 46, both of which are positioned on a left ventricular lead 22. FIG. 16 shows a left ventricular sense between a tip electrode 36, and two ring electrodes 46 and 48, all of which are positioned on a left ventricular lead 22.

Figure 18:
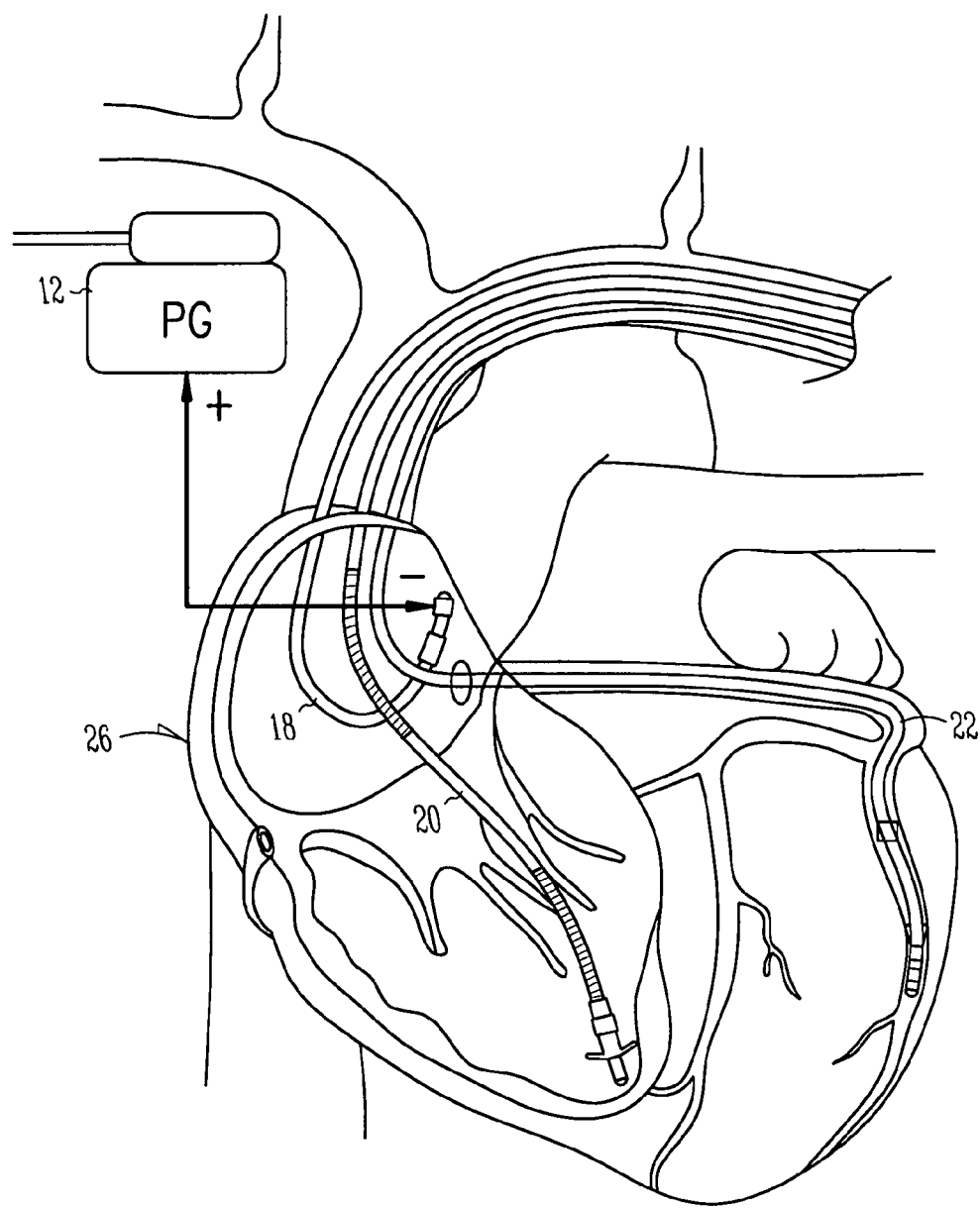
FIGS. 18–19 illustrate pacing vector examples for an atrial lead.
Figure 19:
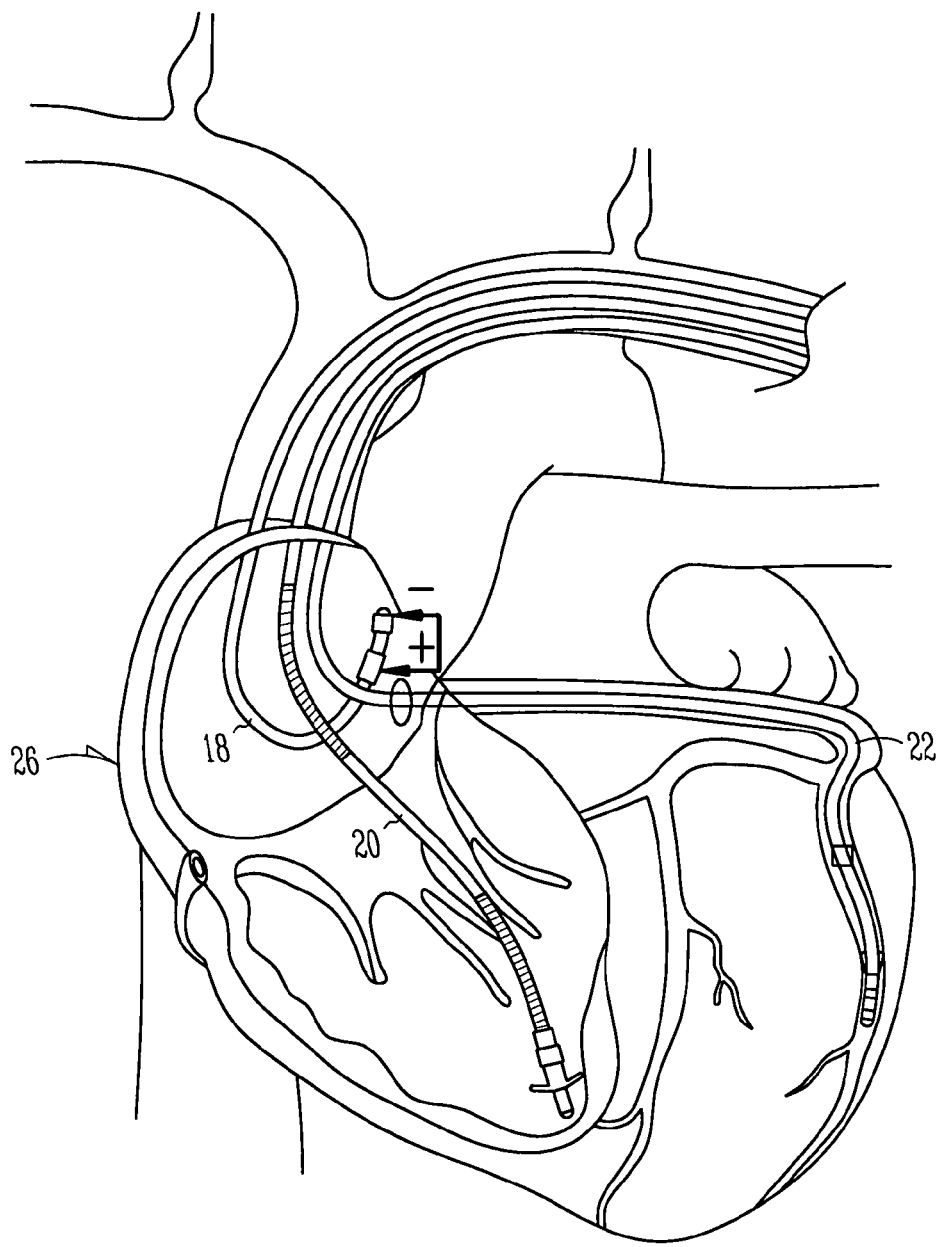

FIGS. 18–19 illustrate pacing vector examples for an atrial lead. FIG. 18 shows an atrial pace from a tip electrode on an atrial lead 18 to the can or medical device 12. FIG. 19 shows an atrial pace from a tip electrode to a ring electrode, both of which are on an atrial lead 18.

Figure 20:
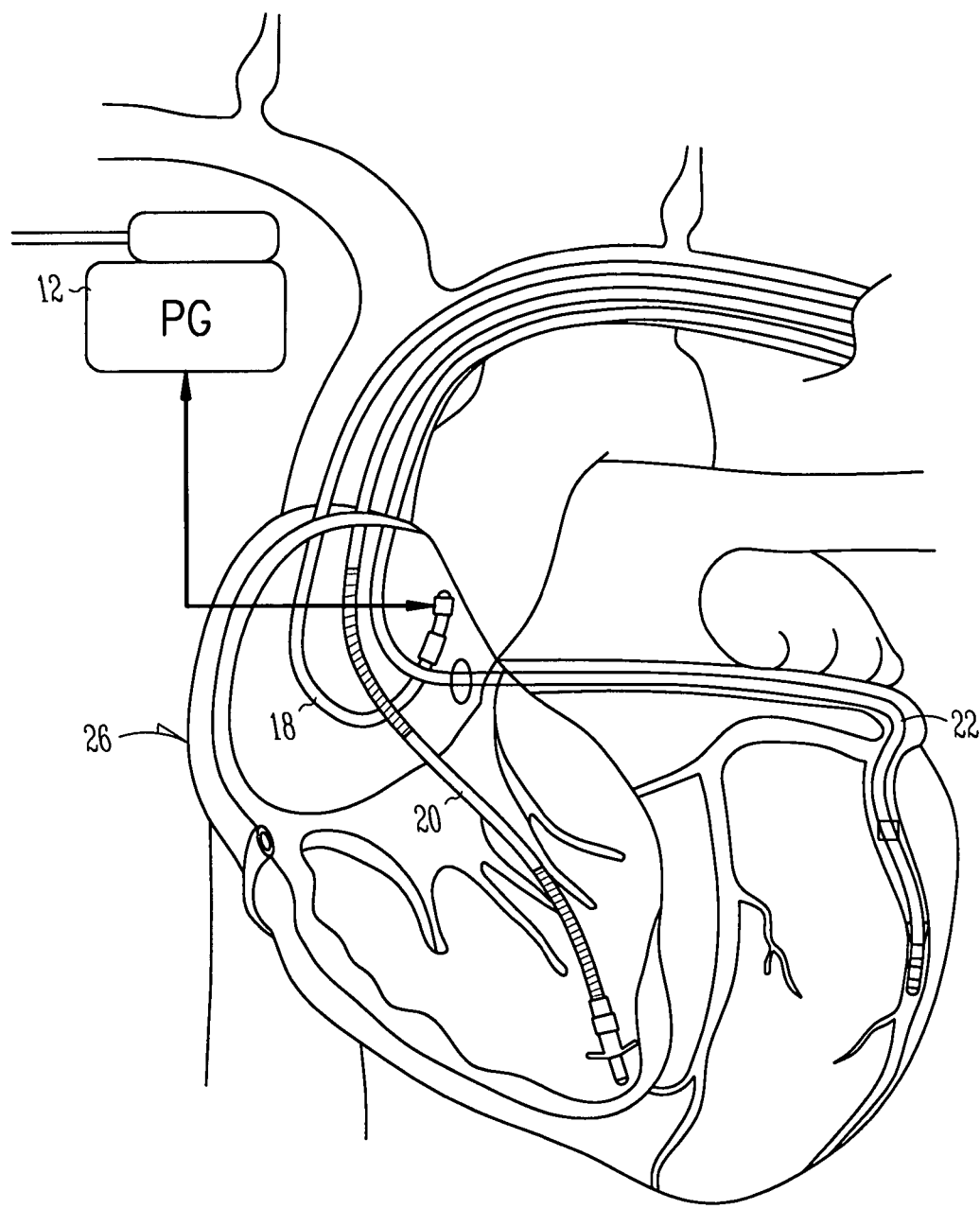
FIGS. 20–21 illustrate sensing vector examples for an atrial lead.
Figure 21:
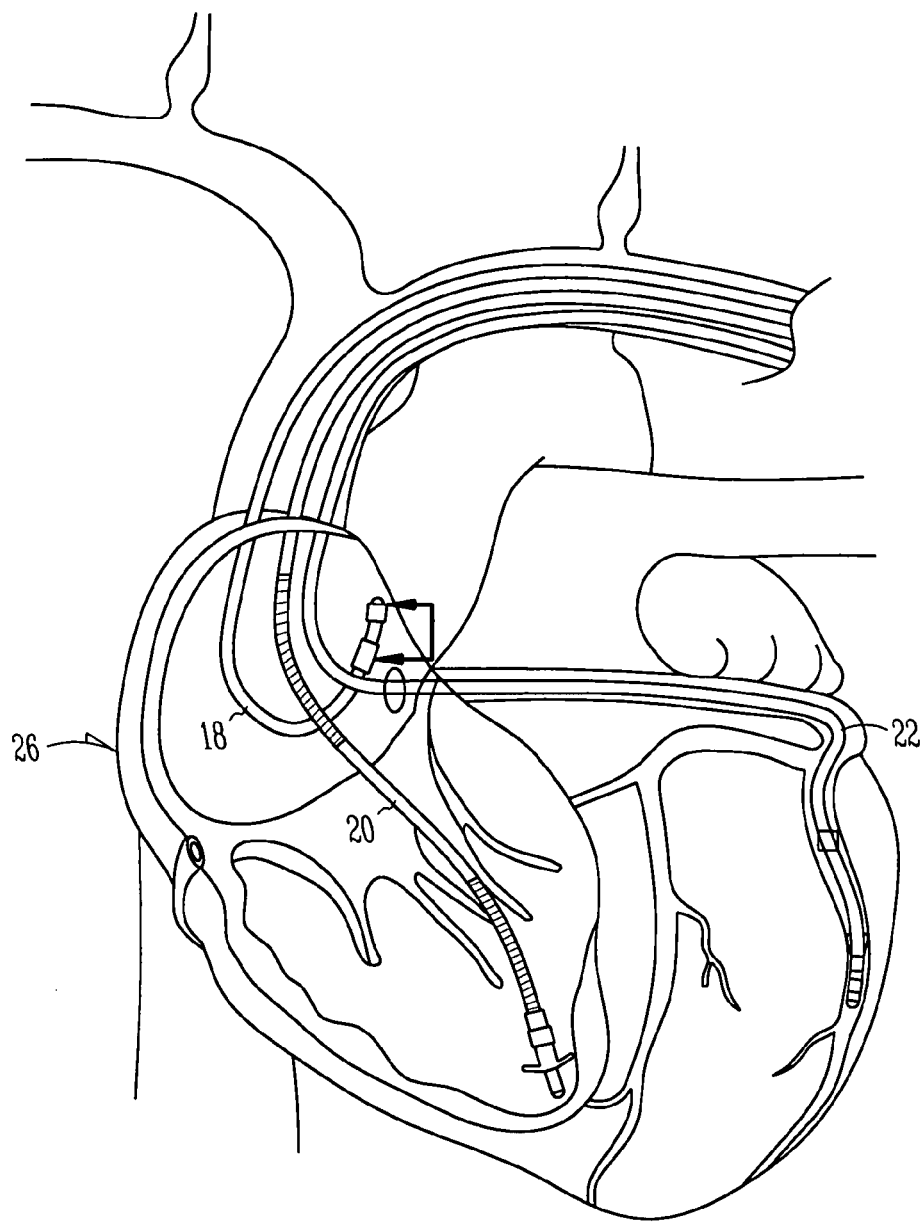

FIGS. 20–21 illustrate sensing vector examples for an atrial lead. FIG. 20 shows an atrial sense between a tip electrode on an atrial lead 18 and the can or medical device. FIG. 21 shows an atrial sense between a tip electrode and a ring electrode, both of which are on an atrial lead 18.

Figure 22:
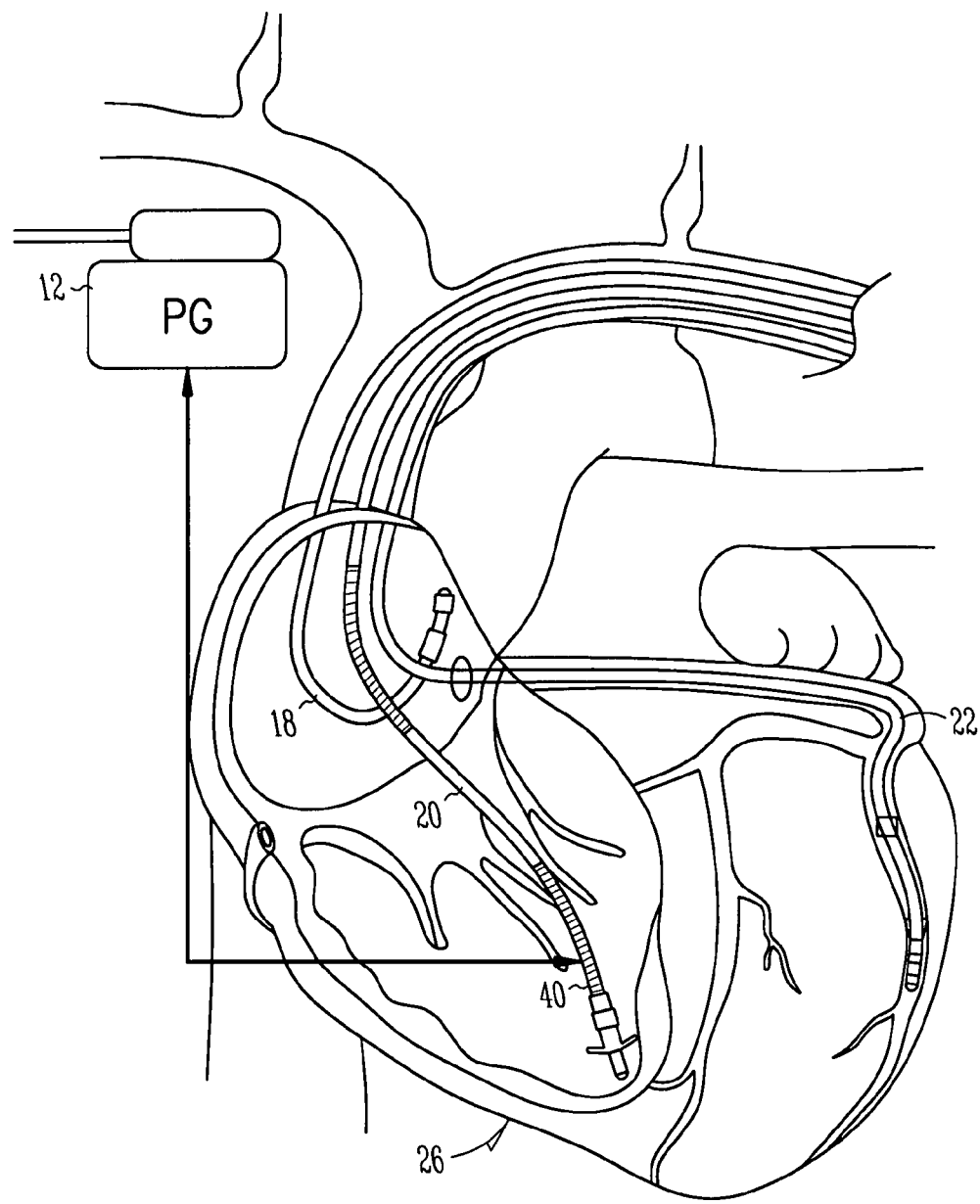
FIGS. 22–23 illustrate defibrillation vector examples.
Figure 23:
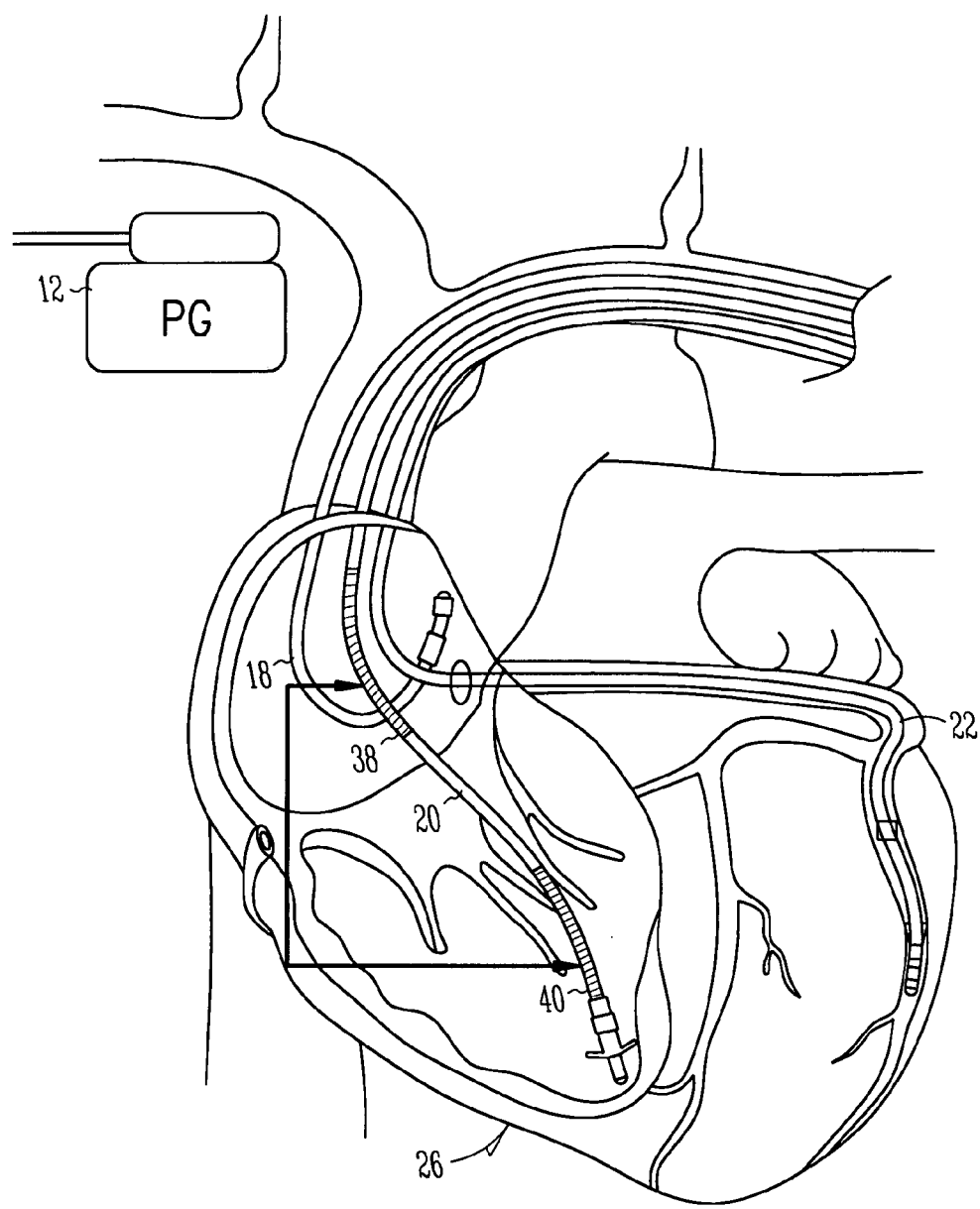

FIGS. 22–23 illustrate defibrillation vector examples. FIG. 22 shows a defibrillation vector between a conductor 40 and the can or medical device 12. FIG. 23 shows a defibrillation vector between a conductor 40 and the coil inductor 38. Although defibrillation pulses have polarity, these illustrated defibrillation vectors do not show a polarity because of the nature of defibrillation vectors. The most common defibrillation types are biphasic which switch polarity half way through the shock, and monophasic which have a fixed polarity that is programmable into the device from the programmer.

Figure 24:
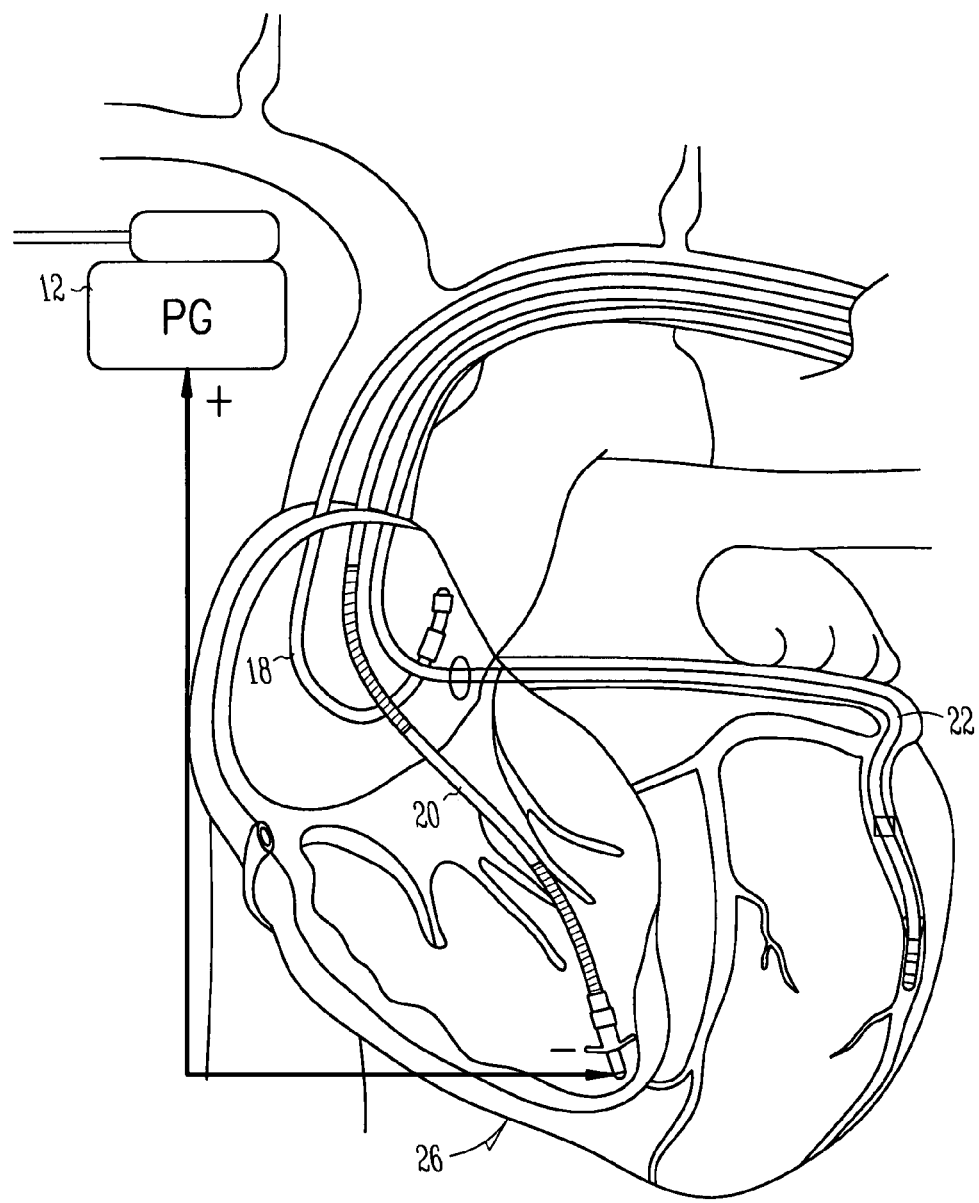
FIGS. 24–25 illustrate pacing vector examples for a right ventricular lead.
Figure 25:
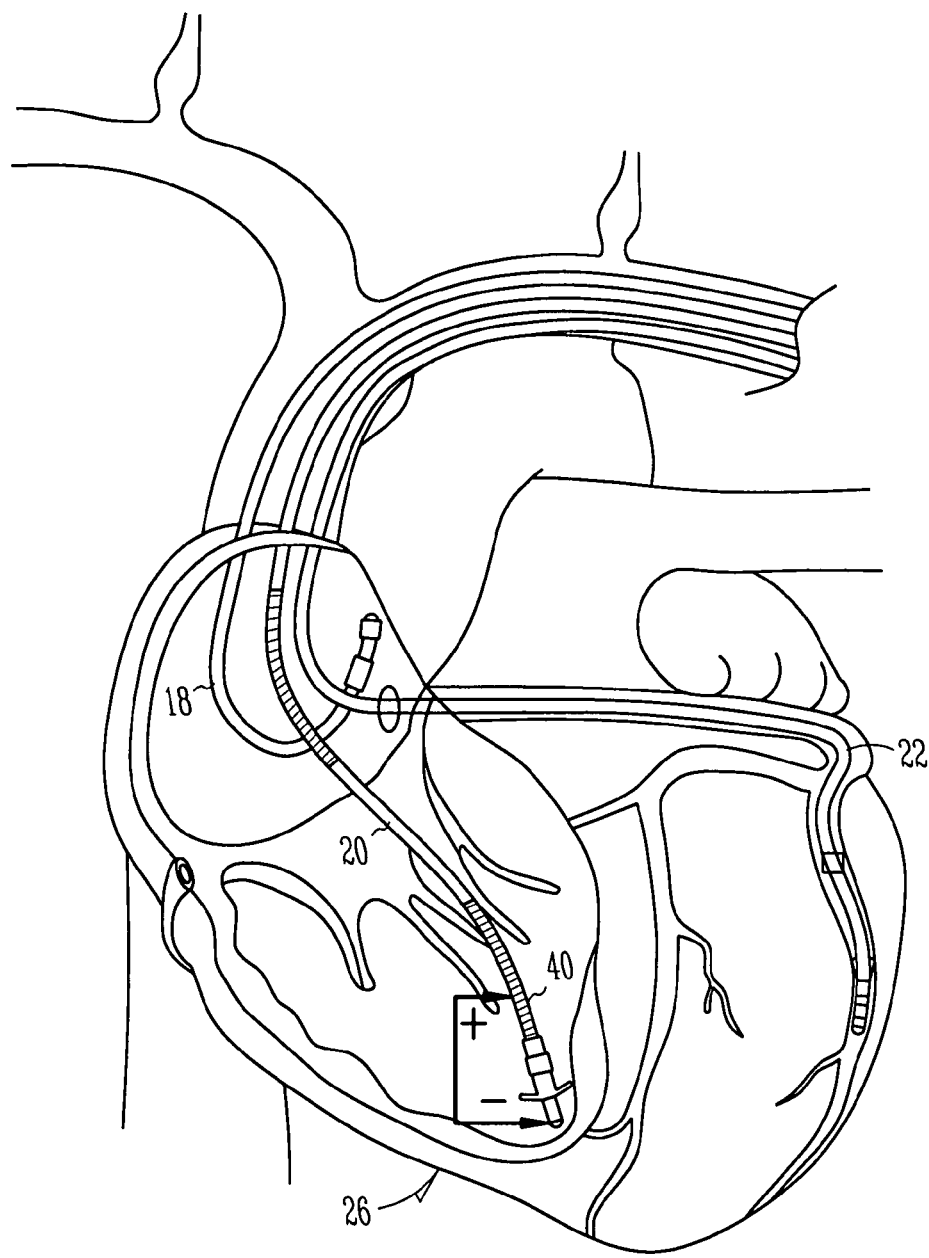

FIGS. 24–25 illustrate pacing vector examples for a right ventricular lead. FIG. 24 shows a right ventricular pace from a tip electrode positioned on a right ventricular lead 20 to a can or medical device 12. FIG. 25 shows a right ventricular pace from a tip electrode to a ring electrode 40, both positioned on a right ventricular lead 20.

Figure 26:
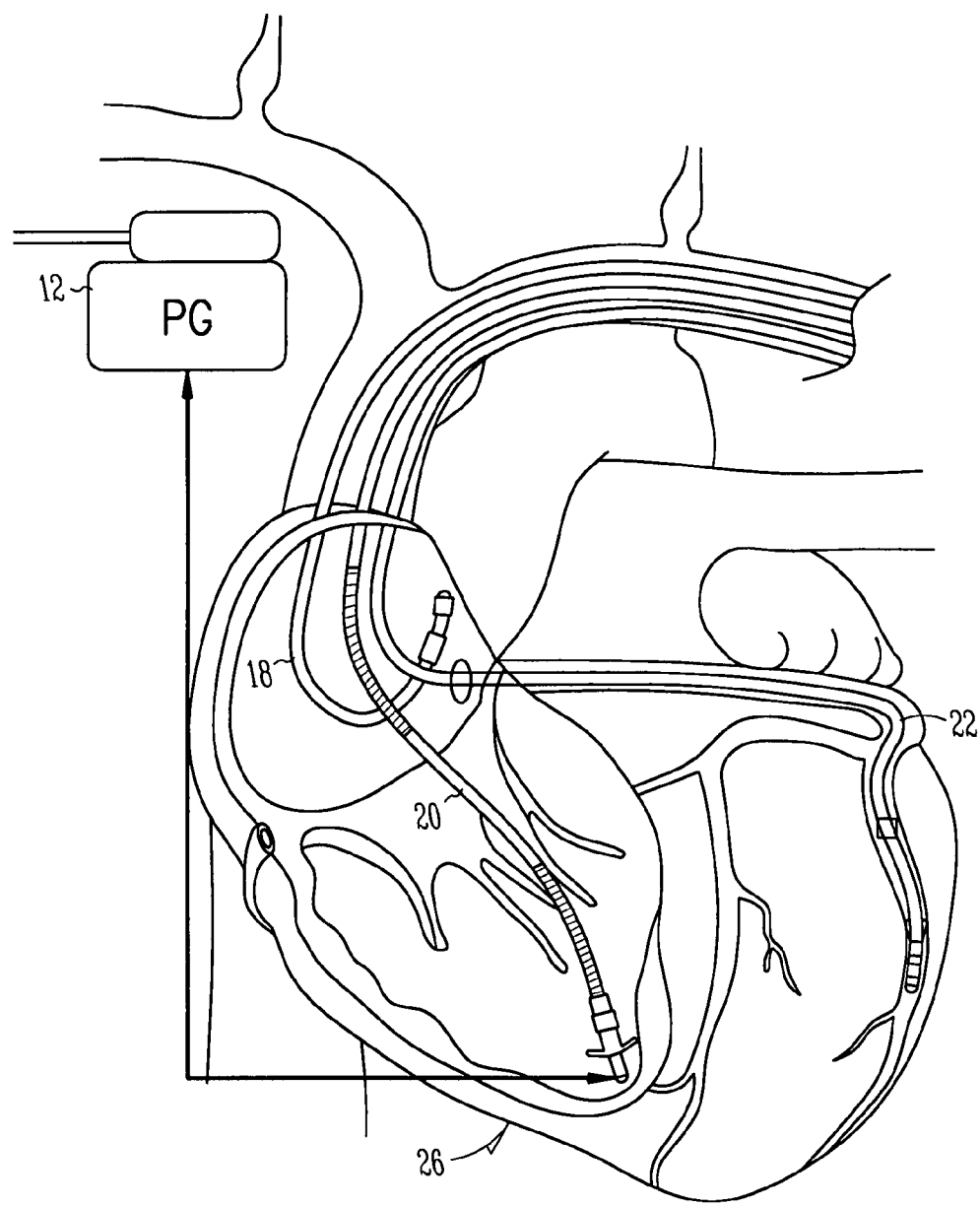
FIGS. 26–27 illustrate sensing vector examples for a right ventricular lead.
Figure 27:
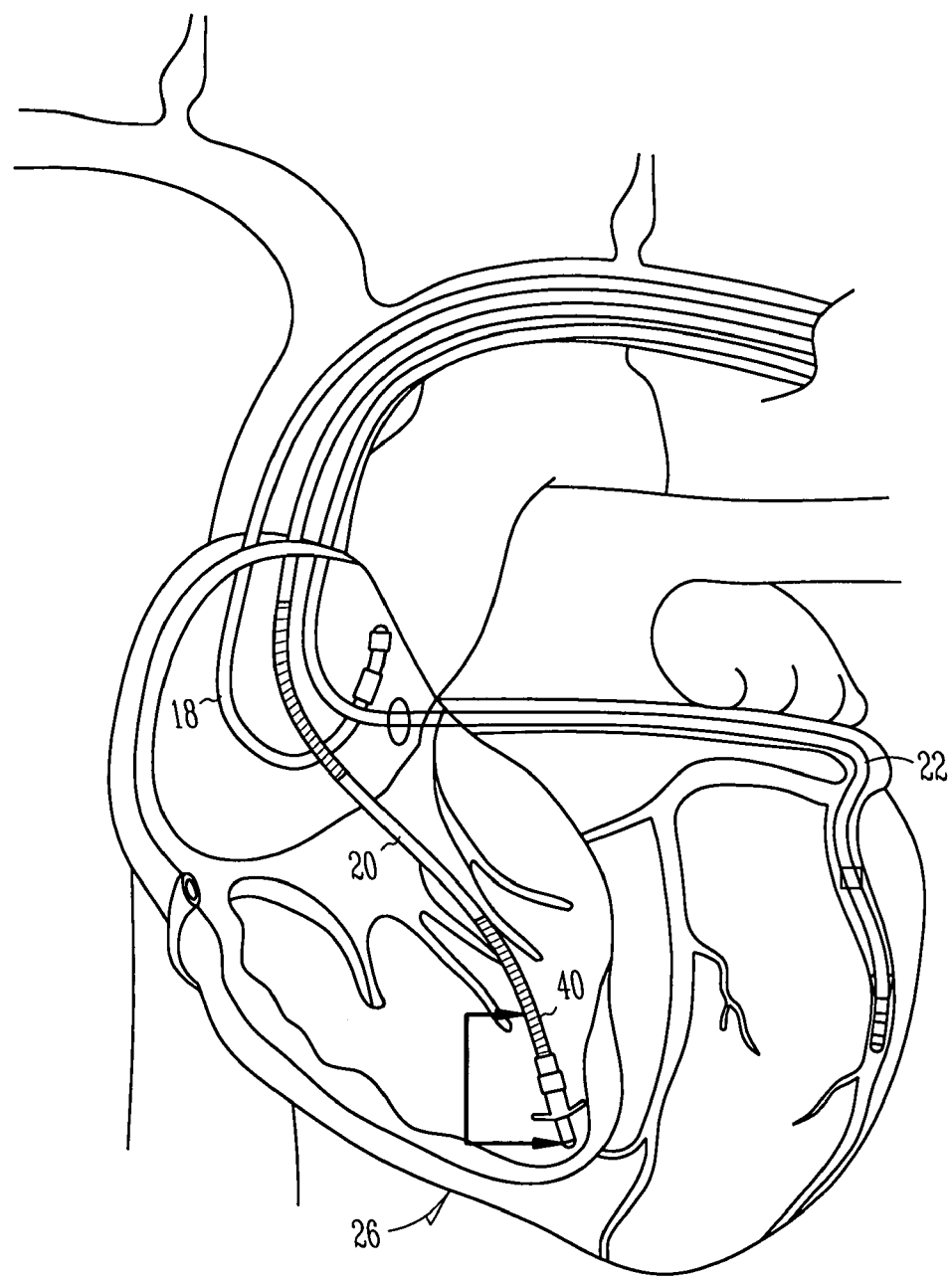

FIGS. 26–27 illustrate sensing vector examples for a right ventricular lead. FIG. 26 shows a right ventricular sense between a tip electrode positioned on a right ventricular lead 20 to a can or medical device. FIG. 27 shows a right ventricular sense between a tip electrode to a ring electrode 40, both positioned on a right ventricular lead 20.

The present invention, as described above, is not limited to any particular chamber of the heart, or combination of chambers, but covers any lead placement inside or outside of the right and left atriums and ventricles, and any vectors that can be formed between the electrode(s).

This application is intended to cover any adaptations or variations of the present invention. It is manifestly intended that this invention be limited only by the claims and equivalents thereof.

What is claimed is:

1. A system, comprising:
an implantable medical device including at least one lead with at least one electrode, the implantable medical device having a programmable electrical configuration for the at least one electrode, the implantable medical device being adapted to apply an electrical signal between the at least one electrode and at least one other electrode of the implantable medical device based on the programmable electrical configuration; and
a processing device adapted to be in communication with the implantable medical device, wherein the processing device provides a graphical display, the graphical display including a representative image of the programmable electrical configuration for the at least one electrode, including a representative image of the electrical signal to be applied between the at least one electrode and the at least one other electrode, wherein the processing device is adapted to provide the graphical display that includes the representative image of the electrical signal between the at least one electrode and the at least one other electrode before the implantable medical device applies the electrical signal between the at least one electrode and the at least one other electrode.

2. The system of claim 1, wherein the representative image includes a representation of an electrode type for each of the at least one electrode.

3. The system of claim 1, wherein the representative image includes a representation of an electrode quantity for each of the at least one lead.

4. The system of claim 1, wherein the representative image includes a representation of a lead position for each of the at least one lead and an electrode position for each of the at least one electrode.

5. The system of claim 1, wherein the medical device is a cardiac stimulus device, and the representative image includes a representation of an arrangement of the at least one lead and the at least one electrode in a heart.

6. The system of claim 1, wherein the representative image includes a representation of a pulse polarity for the programmable electrical configuration.

7. The system of claim 1, wherein the representative image includes a representation of a vector associated with the at least one electrode that is indicative of at least one of a sensing vector and a pulsing vector.

8. The system of claim 1, wherein the representative image includes a representation of a pace vector.

9. The system of claim 1, wherein the representative image includes a representation of a sense vector.

10. The system of claim 1, wherein the representative image includes a representation of a defibrillation vector.

11. The system of claim 1, wherein the representative image includes a color scheme to represent elements of the at least one lead with the at least one electrode, and the programmable electrical configuration.

12. The system of claim 1, wherein the graphical display represents present settings for the programmable electrical configuration, and wherein the present settings are stored in a memory.

13. The system of claim 1, wherein the processing device is adapted to change the programmable electrical configuration, and wherein the graphical display represents present settings and changed settings.

14. The system of claim 1, wherein the processing device includes a screen display for providing the graphical display of the programmable electrical configuration.

15. The system of claim 14, wherein the screen display comprises a monitor.

16. The system of claim 1, wherein the processing device comprises a programmer.

17. The system of claim 1, wherein the processing device comprises a personal computer.

18. A system, comprising:
means for receiving information about an implantable medical device having at least one lead with at least one electrode in a programmable electrical configuration, the implantable medical device being adapted to apply an electrical signal between the at least one electrode and at least one other electrode of the implantable medical device based on the programmable electrical configuration; and
means for graphically representing the programmable electrical configuration as a representative image of the programmable electrical configuration for the at least one electrode, including a representative image of the electrical signal to be applied between the at least one electrode and the at least one other electrode, wherein the means for graphically representing the configuration is adapted to provide the representative image of the electrical signal between the at least one electrode and the at least one other electrode before the implantable medical device applies the electrical signal between the at least one electrode and the at least one other electrode.

19. The system of claim 18, further comprising means for storing present settings for the programmable electrical configuration in a memory, wherein the means for receiving information includes means for retrieving the present settings for the programmable electrical configuration from the memory.

20. The system of claim 18, further comprising means for changing the programmable electrical configuration, wherein the means for graphically representing the programmable electrical configuration includes means for displaying both present settings and changed settings for the programmable electrical configuration.

21. The system of claim 18, wherein the means for graphically representing the programmable electrical configuration includes means for representing an electrode type in the representative image of the programmable electrical configuration for the at least one electrode.

22. The system of claim 18, wherein the means for graphically representing the programmable electrical configuration includes means for representing a lead position and an electrode position type in the representative image of the programmable electrical configuration for the at least one electrode.

23. The system of claim 18, wherein the means for graphically representing the programmable electrical configuration includes means for representing a pulse polarity type in the representative image of the programmable electrical configuration for the at least one electrode.

24. The system of claim 18, wherein the means for graphically representing the programmable electrical configuration includes means for representing a vector type in the representative image of the programmable electrical configuration for the at least one electrode.

25. The system of claim 24, wherein the means for representing the vector comprises means for representing a pace vector type in the representative image of the programmable electrical configuration for the at least one electrode.

26. The system of claim 24, wherein the means for representing the vector comprises means for representing a sense vector type in the representative image of the programmable electrical configuration for the at least one electrode.

27. The system of claim 24, wherein the means for representing the vector comprises means for representing a defibrillation vector type in the representative image of the programmable electrical configuration for the at least one electrode.

28. A device, comprising:
circuit for communicating with an implantable medical device having at least one lead with at least one electrode, wherein the at least one electrode has a programmable electrical configuration, the implantable medical device being adapted to apply an electrical signal between the at least one electrode and at least one other electrode of the implantable medical device based on the programmable electrical configuration; and
a display for graphically representing the programmable electrical configuration of the at least one electrode for the implantable medical device as a representative image, including a representative image of the electrical signal to be applied between the at least one electrode and the at least one other electrode, wherein the circuitry is adapted to provide the display that includes the representative image of the electrical signal between the at least one electrode and the at least one other electrode before the implantable medical device applies the electrical signal between the at least one electrode and the at least one other electrode.

29. The device of claim 28, wherein the representative image includes a lead representation and an electrode representation.

30. The device of claim 28, wherein the lead representation includes a lead position representation.

31. The device of claim 28, wherein the electrode representation includes an electrode type representation.

32. The device of claim 28, wherein the electrode representation includes an electrode position representation.

33. The device of claim 28, wherein the representative image further includes a pulse polarity representation.

34. The device of claim 28, wherein the representative image further includes a vector representation associated with the programmable electrical configuration.

35. The device of claim 34, wherein the vector representation comprises a pace vector representation.

36. The device of claim 34, wherein the vector representation comprises a sense vector representation.

37. The device of claim 34, wherein the vector representation comprises a defibrillation vector representation.

38. The device of claim 28, wherein the display is a monitor.

39. A computer-readable medium encoded with a software program for providing a graphical display of a lead configuration for an implantable medical device having at least one lead with at least one electrode in a programmable electrical configuration, the implantable medical device being adapted to apply an electrical signal between the at least one electrode and at least one other electrode of the implantable medical device based on the programmable electrical configuration, the software program executing the following:

receiving information about the lead configuration and the programmable electrical configuration; and graphically representing the lead configuration and the programmable electrical configuration as a representative image, including a representative image of the electrical signal to be applied between the at least one electrode and the at least one other electrode, wherein the representative image of the electrical signal between the at least one electrode and the at least one other electrode is graphically represented before the implantable medical device applies the electrical signal between the at least one electrode and the at least one other electrode.

40. The computer-readable medium of claim 39, wherein receiving information includes receiving both a present setting and a changed setting for the programmable electrical configuration, and after the step of graphically representing the programmable electrical configuration, the software program further executes:

receiving user verification that the changed setting is acceptable; and accepting the changed setting.

41. The computer-readable medium of claim 39, wherein graphically representing the programmable electrical configuration includes graphically displaying a lead representation and an electrode representation in the representative image.

42. The computer-readable medium of claim 39, wherein graphically representing the programmable electrical configuration includes graphically displaying a pulse polarity in the representative image.

43. The computer-readable medium of claim 39, wherein graphically representing the programmable electrical configuration includes graphically displaying a vector in the representative image.

44. The computer-readable medium of claim 43, wherein the vector comprises a pace vector in the representative image.

45. The computer-readable medium of claim 43, wherein the vector comprises a sense vector in the representative image.

46. The computer-readable medium of claim 43, wherein the vector comprises a defibrillation vector in the representative image.

47. A method, comprising:

receiving information for an implantable medical device having at least one lead with at least one electrode, the implantable medical device having a programmable electrical configuration for the at least one electrode, the implantable medical device being adapted to apply an electrical signal between the at least one electrode and at least one other electrode of the implantable medical device based on the programmable electrical configuration; and presenting a graphical representation of the programmable electrical configuration as a representative image, including a representative image of the electrical signal to be applied between the at least one electrode and the at least one other electrode, wherein the graphical representation, including the representative image of the electrical signal between the at least one electrode and the at least one other electrode, is presented before the implantable medical device applies the electrical signal between the at least one electrode and the at least one other electrode.

48. The method of claim 47, wherein receiving information includes retrieving the information from a memory.

49. The method of claim 47, wherein the implantable medical device is a cardiac stimulus device, and wherein presenting a graphical representation of the programmable electrical configuration includes graphically representing an arrangement of the at least one lead in a heart.

50. The method of claim 47, wherein presenting a graphical representation of the programmable electrical configuration includes graphically representing an electrode type in the representative image.

51. The method of claim 47, wherein presenting a graphical representation of the programmable electrical configuration includes graphically representing a pulse polarity in the representative image.

52. The method of claim 47, wherein presenting a graphical representation of the programmable electrical configuration includes graphically representing a vector in the representative image.

53. The method of claim 52, wherein the vector comprises a pace vector.

54. The method of claim 52, wherein the vector comprises a sense vector.

55. The method of claim 52, wherein the vector comprises a defibrillation vector.

56. The method of claim 47, wherein presenting a graphical representation includes presenting the representative image to a screen display.

57. The method of claim 47, wherein the method further comprises programming a change in the programmable electrical configuration, and wherein presenting a graphical representation of the programmable electrical configuration includes presenting both current settings and changed settings for the programmable electrical configuration.

* * * * *

UNITED STATES PATENT AND TRADEMARK OFFICE
CERTIFICATE OF CORRECTION

PATENT NO. : 7,236,826 B2  Page 1 of 1
APPLICATION NO. : 09/738400
DATED : June 26, 2007
INVENTOR(S) : Lindh et al.

It is certified that error appears in the above-identified patent and that said Letters Patent is hereby corrected as shown below:

On the Title page, in field (75), in "Inventors", in column 1, line 1, delete "Little Canada" and insert -- Maple Grove --, therefor.

On the Title page, in field (75), in "Inventors", in column 1, lines 3-4, delete "White Bear Lake, MN (US)" and insert -- Overijse, Belgium --, therefor.

In column 14, line 29, in Claim 28, delete "circuit" and insert -- circuitry --, therefor.

Signed and Sealed this

Fourteenth Day of August, 2007

JON W. DUDAS
*Director of the United States Patent and Trademark Office*